United States Patent
Yang et al.

(10) Patent No.: US 10,351,586 B2
(45) Date of Patent: *Jul. 16, 2019

(54) CYTIDINE DERIVATIVE DIMERS AND APPLICATIONS THEREOF

(71) Applicants: CHANGZHOU FANGYUAN PHARMACEUTICAL CO., LTD, Changzhou (CN); INNER MONGOLIA PUYIN PHARMACEUTICAL CO., LTD, Chifeng (CN)

(72) Inventors: Daria Yang, Changzhou (CN); Haidong Wang, Changzhou (CN); Hui-Juan Wang, Changzhou (CN)

(73) Assignees: CHANGZHOU FANGYUAN PHARMACEUTICAL CO., LTD, Changzhou (CN); INNER MONGOLIA PUYIN PHARMACEUTICAL CO., LTD, Chifeng (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,980

(22) Filed: Dec. 14, 2017

(65) Prior Publication Data
US 2018/0105550 A1 Apr. 19, 2018

Related U.S. Application Data

(63) Continuation of application No. 14/624,513, filed on Feb. 17, 2015, now Pat. No. 9,862,741.

(30) Foreign Application Priority Data

Nov. 17, 2014 (CN) .......................... 2014 1 0652724

(51) Int. Cl.
*C07H 19/06* (2006.01)
*C07H 1/00* (2006.01)
*A61P 35/00* (2006.01)

(52) U.S. Cl.
CPC .............. *C07H 19/06* (2013.01); *A61P 35/00* (2018.01); *C07H 1/00* (2013.01)

(58) Field of Classification Search
CPC .................................. C07H 19/06; C07H 1/00
See application file for complete search history.

(56) References Cited

U.S. PATENT DOCUMENTS 9,862,741 B2 * 1/2018 Yang ...................... C07H 19/06
2016/0137684 A1 5/2016 Yang et al.

FOREIGN PATENT DOCUMENTS

WO 2004041203 A2 5/2004
WO 2014078295 A1 5/2014
WO WO-2016188943 A1 * 12/2016 .............. C07H 19/10

OTHER PUBLICATIONS

Guo et al., Selective Protection of 2',2'-Difluorodeoxycytidine (Gemcitabine), J. Org. Chem., 64 (22), 8319-8322 (1999).*
The World Intellectual Property Organization (WIPO) International Search Report for PCT/CN2015/081138 dated Sep. 16, 2015 pp. 1-7.
Kazuhiko Kondo, et al., "Studies on Biologically Active Nucleosides and Nucleotides. 5. Synthesis and Antitumor Activity of Some 2,2'-Anhydro-1-(3',5'-di-O-acyl-β-D-arabinofuranosyl)cytosine Salts and 2,2'-Anhydro-1-(3'-O-acyl-β-D-arabinofuranoxyl)cytosine 5'-Phosphates", Journal of Medicinal Chemistry, Jun. 1, 1979 (Jun. 1, 1979), vol. 22, No. 6, pp. 639-646, the whole document, especially Scheme II, compound 20.
Thodoros Karampelas, et al., "GnRH-Gemcitabine Conjugates for the Treatment of Androgen-Independent Prostate Cancer: Pharmacokinetic Enhancements Combined with Targeted Drug Delivery", Bioconjugate Chemistry, Mar. 24, 2014 (Mar. 24, 2014), vol. 25, No. 4, pp. 1-22, the whole document, especially Scheme 1, compounds 2 and 3.

* cited by examiner

*Primary Examiner* — Lawrence E Crane
(74) *Attorney, Agent, or Firm* — Anova Law Group, PLLC

(57) ABSTRACT

The present disclosure provides cytidine derivative dimers, salts and compositions of the cytidine derivative dimers, and methods of making and using the cytidine derivative dimers. The disclosed compounds are useful for treating a neoplasm in mammalian subjects. The cytidine derivative dimer has the following general formula (I).

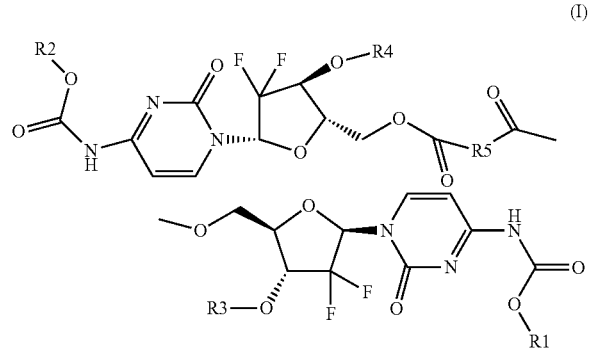

where R1 is $C_1$-$C_{10}$ alkyl, $C_1$-$C_{10}$ substituted alkyl, —$(CH_2)_n$-Ph, or substituted —$(CH_2)_n$-Ph; R2 is $C_1$-$C_{10}$ alkyl, $C_1$-$C_{10}$ substituted alkyl, —$(CH_2)_n$-Ph, or substituted —$(CH_2)_n$-Ph; R3 is hydrogen, alkoxycarbonyl or substituted alkoxycarbonyl; R4 is hydrogen, alkoxycarbonyl or substituted alkoxycarbonyl; and R5 is —$(CH_2)_n$—, substituted —$(CH_2)_n$—, or —$(CH_2)_{n1}$—O—$(CH_2)_{n2}$-Ph-, where n, n1, and n2 are an integer from 0 to 3. The disclosed cytidine derivative dimers/salts provide high anti-tumor activity with low toxicity and are useful for treating cancers.

12 Claims, 5 Drawing Sheets

CYTIDINE DERIVATIVE DIMERS AND APPLICATIONS THEREOF

CROSS-REFERENCES TO RELATED APPLICATIONS

This application is a continuation application of U.S. patent application Ser. No. 14/624,513, filed on Feb. 17, 2015, and granted on Jan. 9, 2018 with U.S. Pat. No. 9,862,741. U.S. patent application Ser. No. 14/624,513 claims the priority of Chinese Patent Application No. 201410652724.4, entitled "Cytidine Derivative Dimer and Applications thereof", filed on Nov. 17, 2014, the entire content of which is incorporated herein by reference.

FIELD OF THE DISCLOSURE

The present disclosure relates to the field of antitumor compounds and, more particularly, relates to cytidine derivative dimers, salts and compositions of the cytidine derivative dimers, and methods of making and using the cytidine derivative dimers for treating various cancers.

BACKGROUND

Cancer is one of the common diseases that threaten human health. The mortality rate of cancer ranks the highest among other diseases. Currently clinical antitumor drugs face prominent toxicity issues in chemotherapy. Nowadays, an important topic on antitumor drugs is to improve the therapeutic effect while reducing the toxicity of the drugs at the same time.

Existing cytidine compounds are mainly used for treating blood tumors. Certain cytidine compounds are also used for solid tumors. However, problems arise due to high toxicity, narrow scope of application and poor therapeutic effect of these compounds. Further, human cancer is prone to producing drug resistance to existing cytidine compounds, resulting in failure of treatment and tumor recurrence.

The disclosed method and system are directed to solve one or more problems set forth above and other problems.

BRIEF SUMMARY OF THE DISCLOSURE

The technical problem to be solved by the present disclosure is to provide a series of cytidine derivative dimers and applications thereof with high efficacy, high anti-tumor activity and low toxicity for treatment of various types of cancers.

One aspect of the present disclosure provides a cytidine derivative dimer of formula (I):

R1 in formula (I) is $C_1$-$C_{10}$ alkyl, $C_1$-$C_{10}$ substituted alkyl, —$(CH_2)_n$-Ph, or substituted —$(CH_2)_n$-Ph, where n is an integer from 0 to 10, and Ph is phenyl. A carbon chain of the $C_1$-$C_{10}$ substituted alkyl is independently substituted by a substituent selected from the group consisting of halogen, cyano group, nitro group, amino group, hydroxyl group, carboxyl group, and a combination thereof. A carbon chain or a phenyl ring of the substituted —$(CH_2)_n$-Ph (where n is an integer from 0 to 10) is independently substituted by a substituent selected from the group consisting of halogen, cyano group, nitro group, amino group, hydroxyl group, carboxyl group, and a combination thereof.

R2 in formula (I) is $C_1$-$C_{10}$ alkyl, $C_1$-$C_{10}$ substituted alkyl, —$(CH_2)_n$-Ph, or substituted —$(CH_2)_n$-Ph, where n is an integer from 0 to 10, and Ph is phenyl. A carbon chain of the $C_1$-$C_{10}$ substituted alkyl is independently substituted by a substituent selected from the group consisting of halogen, cyano group, nitro group, amino group, hydroxyl group, carboxyl group, and a combination thereof. A carbon chain or a phenyl ring of the substituted —$(CH_2)_n$-Ph is independently substituted by a substituent selected from the group consisting of halogen, cyano group, nitro group, amino group, hydroxyl group, carboxyl group, and a combination thereof.

R3 in formula (I) is hydrogen, alkoxycarbonyl or substituted alkoxycarbonyl, wherein a substituent of the substituted alkoxycarbonyl is selected from the group consisting of halogen, cyano group, nitro group, amino group, hydroxyl group, carboxyl group and a combination thereof.

R4 in formula (I) is hydrogen, alkoxycarbonyl or substituted alkoxycarbonyl, wherein a substituent of the substituted alkoxycarbonyl is selected from the group consisting of halogen, cyano group, nitro group, amino group, hydroxyl group, carboxyl group and a combination thereof.

R5 in formula (I) is —$(CH_2)_n$—, n being an integer from 1 to 15; or substituted —$(CH_2)_n$— with a substituent on a carbon chain thereof, n being an integer from 1 to 15. The substituent can be selected from the group consisting of phenyl group, substituted phenyl group, cyano group, nitro group, amino group, hydroxyl group, carboxyl group, and a combination thereof. Alternatively, R5 can be —$(CH_2)_n$—$X_1$—$X_2$—, where $X_1$ is O or S, $X_2$ is —$(CH_2)_n$-Ph-, pyrimidyl, pyranyl, imidazolyl, pyrazinyl, or pyridyl, and n is an integer from 0 to 3.

Another aspect of the present disclosure provides a tumor inhibiting drug including the disclosed cytidine derivative dimer or a salt form thereof.

Another aspect of the present disclosure provides a pharmaceutical composition, including: a cytidine derivative dimer or a pharmaceutically acceptable salt thereof as an active ingredient; and one or more of medicinal carriers and excipients, where the cytidine derivative dimer is represented by formula (I).

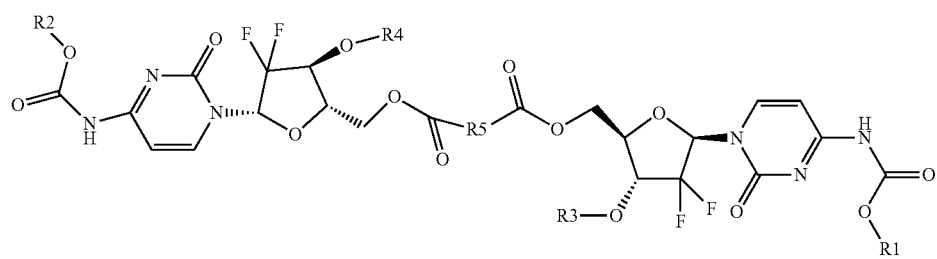

(I)

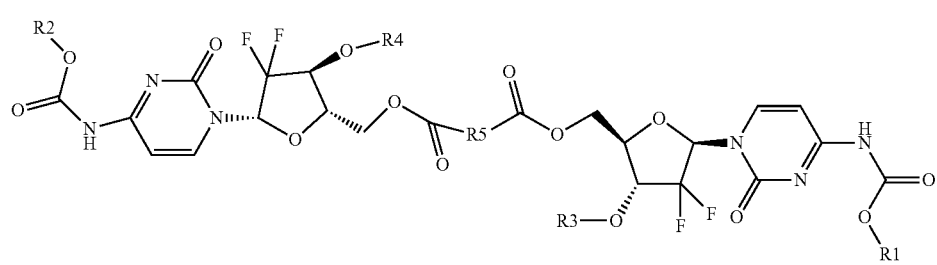

(I)

R1 in formula (I) is $C_1$-$C_{10}$ alkyl, $C_1$-$C_{10}$ substituted alkyl, —$(CH_2)_n$-Ph, or substituted —$(CH_2)_n$-Ph, where n is an integer from 0 to 10, and Ph is phenyl. A carbon chain of the $C_1$-$C_{10}$ substituted alkyl is independently substituted by a substituent selected from the group consisting of halogen, cyano group, nitro group, amino group, hydroxyl group, carboxyl group, and a combination thereof. A carbon chain or a phenyl ring of the substituted —$(CH_2)_n$-Ph is independently substituted by a substituent selected from the group consisting of halogen, cyano group, nitro group, amino group, hydroxyl group, carboxyl group, and a combination thereof.

R2 in formula (I) is $C_1$-$C_{10}$ alkyl, $C_1$-$C_{10}$ substituted alkyl, —$(CH_2)_n$-Ph, or substituted —$(CH_2)_n$-Ph, where n is an integer from 0 to 10, and Ph is phenyl. A carbon chain of the $C_1$-$C_{10}$ substituted alkyl is independently substituted by a substituent selected from the group consisting of halogen, cyano group, nitro group, amino group, hydroxyl group, carboxyl group, and a combination thereof. A carbon chain or a phenyl ring of the substituted —$(CH_2)_n$-Ph is independently substituted by a substituent selected from the group consisting of halogen, cyano group, nitro group, amino group, hydroxyl group, carboxyl group, and a combination thereof.

R3 in formula (I) is hydrogen, alkoxycarbonyl or substituted alkoxycarbonyl, wherein a substituent of the substituted alkoxycarbonyl is selected from the group consisting of halogen, cyano group, nitro group, amino group, hydroxyl group, carboxyl group and a combination thereof.

R4 in formula (I) is hydrogen, alkoxycarbonyl or substituted alkoxycarbonyl, wherein a substituent of the substituted alkoxycarbonyl is selected from the group consisting of halogen, cyano group, nitro group, amino group, hydroxyl group, carboxyl group and a combination thereof.

R5 in formula (I) is —$(CH_2)_n$—, n being an integer from 1 to 15; or substituted —$(CH_2)_n$— with a substituent on a carbon chain thereof, n being an integer from 1 to 15. The substituent can be selected from the group consisting of phenyl group, substituted phenyl group, cyano group, nitro group, amino group, hydroxyl group, carboxyl group, and a combination thereof. Alternatively, R5 can be —$(CH_2)_n$—$X_1$—$X_2$—, where $X_1$ is O or S, $X_2$ is —$(CH_2)_n$-Ph-, pyrimidyl, pyranyl, imidazolyl, pyrazinyl, or pyridyl, and n is an integer from 0 to 3.

Another aspect of the present disclosure provides a method for preparing a cytidine derivative dimer as follows. A compound having a general formula (II) is prepared first.

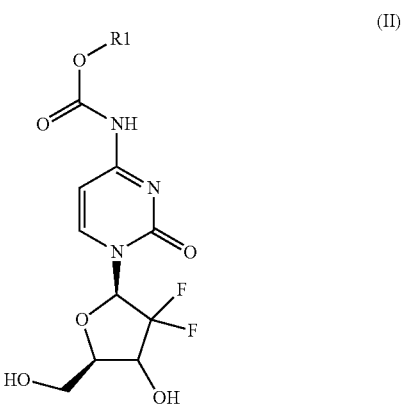

(II)

Further, a compound having a general formula (III) is prepared. The compound having the general formula (II) is mixed with sodium carbonate to add to a system including 1,4-dioxane and water. $(Boc)_2O$ is further added for a reaction. When the reaction is measured to be completed to provide a reaction product, the reaction product is extracted and washed, and then dried and concentrated to form a dried solid under a reduced pressure.

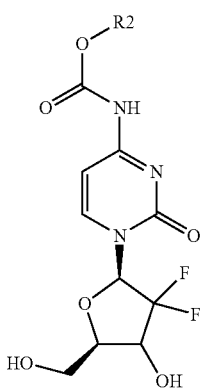

(III)

The dried solid is added into chloroform. Pyridine and dianhydrides $R_5(CO)_2O$ are also added into the chloroform for an overnight reaction to provide a reaction product. The reaction product is concentrated to obtain a viscous oil. The viscous oil is purified by column chromatography to obtain a compound with a general formula (IV).

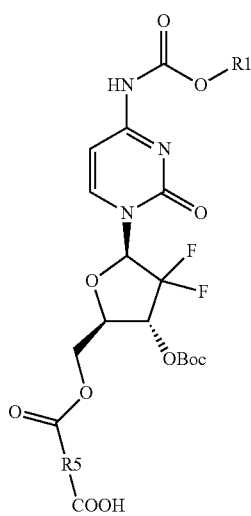

(IV)

R1 in formula (II) and (IV) is $C_1$-$C_{10}$ alkyl, $C_1$-$C_{10}$ substituted alkyl, —$(CH_2)_n$-Ph, or substituted —$(CH_2)_n$-Ph, where n is an integer from 0 to 10, and Ph is phenyl. A carbon chain of the $C_1$-$C_{10}$ substituted alkyl is independently substituted by a substituent selected from the group consisting of halogen, cyano group, nitro group, amino group, hydroxyl group, carboxyl group, and a combination thereof. A carbon chain or a phenyl ring of the substituted —$(CH_2)_n$-Ph is independently substituted by a substituent selected from the group consisting of halogen, cyano group, nitro group, amino group, hydroxyl group, carboxyl group, and a combination thereof.

R2 in formula (III) is $C_1$-$C_{10}$ alkyl, $C_1$-$C_{10}$ substituted alkyl, —$(CH_2)_n$-Ph, or substituted —$(CH_2)_n$-Ph, where n is an integer from 0 to 10, and Ph is phenyl. A carbon chain of the $C_1$-$C_{10}$ substituted alkyl is independently substituted by a substituent selected from the group consisting of halogen, cyano group, nitro group, amino group, hydroxyl group, carboxyl group, and a combination thereof. A carbon chain or a phenyl ring of the substituted —$(CH_2)_n$-Ph is independently substituted by a substituent selected from the group consisting of halogen, cyano group, nitro group, amino group, hydroxyl group, carboxyl group, and a combination thereof.

R5 in formula (IV) is —$(CH_2)_n$—, n being an integer from 1 to 15; or substituted —$(CH_2)_n$— with a substituent on a carbon chain thereof, n being an integer from 1 to 15. The substituent can be selected from the group consisting of phenyl group, substituted phenyl group, cyano group, nitro group, amino group, hydroxyl group, carboxyl group, and a combination thereof. Alternatively, R5 can be —$(CH_2)_n$—$X_1$—$X_2$—, where $X_1$ is O or S, $X_2$ is —$(CH_2)_n$-Ph-, pyrimidyl, pyranyl, imidazolyl, pyrazinyl, or pyridyl, and n is an integer from 0 to 3.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the disclosure, which are illustrated in the accompanying drawings. Hereinafter, embodiments consistent with the disclosure will be described with reference to drawings. Wherever possible, the same reference numbers will be used throughout the drawings to refer to the same or like parts. It is apparent that the described embodiments are some but not all of the embodiments of the present disclosure. Based on the disclosed embodiment, persons of ordinary skill in the art may derive other embodiments consistent with the present disclosure, all of which are within the scope of the present disclosure.

Figure 1:
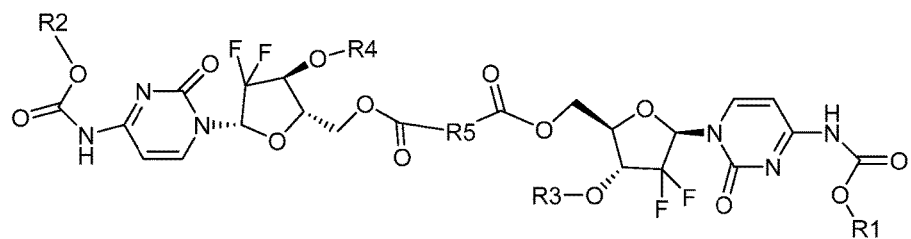
FIG. 1 illustrates an exemplary structural formula of a cytidine derivative dimer consistent with various disclosed embodiments.

As shown in FIG. 1, the present disclosure discloses an exemplary cytidine derivative dimer with a structural formula as formula (I):

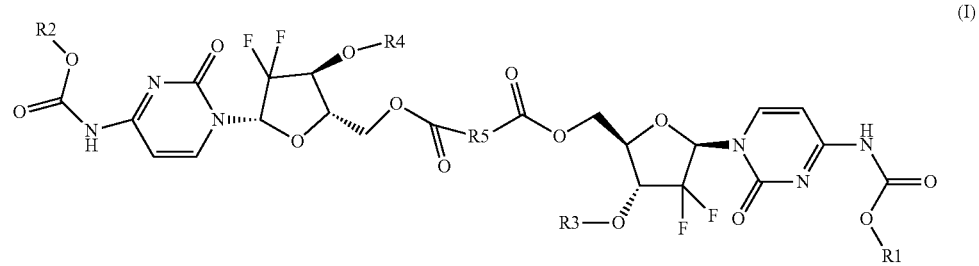

(I)

where R1 can be alkyl containing from 1 to 10 carbon atoms (i.e., $C_1$-$C_{10}$ alkyl), $C_1$-$C_{10}$ substituted alkyl, —$(CH_2)_n$-Ph (where n=0, 1, 2, 3, . . . , 10, and Ph is phenyl), or substituted —$(CH_2)_n$-Ph (where n=0, 1, 2, 3, . . . , 10, and Ph is phenyl). The carbon chain of the substituted alkyl can be independently substituted by one or two or three groups including halogen, cyano group, nitro group, amino group, hydroxyl group, or carboxyl group. The carbon chain or the phenyl ring of the substituted —$(CH_2)_n$-Ph can be independently substituted by one or two or three groups including halogen, cyano group, nitro group, amino group, hydroxyl group, or carboxyl group.

In certain embodiments, R1 can be $C_1$-$C_{10}$ alkyl or —$(CH_2)_n$-Ph (where n=0, 1, 2, 3, . . . , 10). For example, R1 is $C_1$-4 alkyl or —$(CH_2)_n$-Ph (where n=0, 1, 2, 3). In an exemplary embodiment, R1 is n-butyl or benzyl.

R2 in formula (I) can be $C_1$-$C_{10}$ alkyl, $C_1$-$C_{10}$ substituted alkyl, —$(CH_2)_n$-Ph (where n=0, 1, 2, 3, . . . , 10, and Ph is phenyl), or substituted —$(CH_2)_n$-Ph (where n=0, 1, 2, 3, . . . , 10, and Ph is phenyl). The carbon chain of the substituted alkyl can be independently substituted by one or two or three groups including halogen, cyano group, nitro group, amino group, hydroxyl group, or carboxyl group. The carbon chain or the phenyl ring of the substituted —$(CH_2)_n$-Ph can be independently substituted by one or two or three groups including halogen, cyano group, nitro group, amino group, hydroxyl group, or carboxyl group.

In certain embodiments, R2 can be $C_1$-$C_{10}$ alkyl or —$(CH_2)_n$-Ph (where n=0, 1, 2, 3, . . . , 10). For example, R2 is $C_1$-4 alkyl or —$(CH_2)_n$-Ph (where n=0, 1, 2, 3). In an exemplary embodiment, R2 is n-butyl or benzyl.

In certain embodiments, R1 and R2 can be the same.

R3 in formula (I) can be hydrogen, alkoxycarbonyl, or substituted alkoxycarbonyl. The substituent of the substituted alkoxycarbonyl can include, for example, halogen, cyano group, nitro group, amino group, hydroxyl group, or carboxyl group. In certain embodiments, R3 can be H or alkoxycarbonyl. Optionally, R3 is H or n-butoxycarbonyl.

R4 in formula (I) can be hydrogen, alkoxycarbonyl, or substituted alkoxycarbonyl. The substituent of the substituted alkoxycarbonyl can include, for example, halogen, cyano group, nitro group, amino group, hydroxyl group, or carboxyl group. In certain embodiments, R4 can be H or alkoxycarbonyl. Optionally, R4 is H or n-butoxycarbonyl.

In certain embodiments, R3 and R4 can be the same.

R5 in formula (I) can be —$(CH_2)_n$—, where n is from 1 to 15. Alternatively, R5 can be —$(CH_2)$— with substituent(s) on the carbon chain thereof, and the substituent can include halogen, cyano group, nitro group, amino group, hydroxyl group, or carboxyl group. Or R5 can be —$(CH_2)_n$—$X_1$—$X_2$—, where n is 0, 1, 2, or 3; $X_1$ is O or S; and $X_2$ is —$(CH_2)_n$-Ph (n=0, 1, 2, or 3), pyrimidyl, pyranyl, or pyridyl. In certain embodiments, R5 can be —$(CH_2)$— (where n is an integer from 1 to 15) or —$(CH_2)_n$—$X_1$—$X_2$— (where n=0, 1, 2, 3, $X_1$ is O or S and $X_2$ is Ph). For example, R5 is —$(CH_2)_n$— (where n is an integer from 1 to 5) or —$(CH_2)$—O-Ph-. Optionally, R5 is —$(CH_2)_2$— or —$(CH_2)_3$—.

Table 1 lists compounds of exemplary cytidine derivative dimers. However, the cytidine derivative dimers in the present disclosure are not limited to these compounds.

TABLE 1

Compounds of exemplary cytidine derivative dimers.

| Compound No. | Substituent group(s) |
|---|---|
| 101 (D1) | R1 and R2 are n-butyl, R3 and R4 are n-butoxycarbonyl, R5 is —$(CH_2)_3$— |
| 102 | R1 and R2 are n-butyl, R3 and R4 are n-butoxycarbonyl, R5 is —$CH_2$— |
| 103 | R1 and R2 are n-butyl, R3 and R4 are n-butoxycarbonyl, R5 is —$(CH_2)_2$— |
| 104 | R1 and R2 are n-butyl, R3 and R4 are n-butoxycarbonyl, R5 is —$(CH_2)_4$— |
| 105 | R1 and R2 are n-butyl, R3 and R4 are n-butoxycarbonyl, R5 is —$(CH_2)_5$— |
| 106 | R1 and R2 are tert-butyl, R3 and R4 are n-butoxycarbonyl, R5 is —$(CH_2)_3$— |
| 107 (D2) | R1 and R2 are n-butyl, R3 and R4 are H, R5 is —$(CH_2)_3$— |
| 108 | R1 and R2 are n-butyl, R3 and R4 are H, R5 is —$(CH_2)_2$— |
| 109 | R1 and R2 are n-butyl, R3 and R4 are H, R5 is —$(CH_2)_2$—O—Ph— |
| 110 | R1 and R2 are n-butyl, R3 and R4 are H, R5 is —$(CH_2)$—O—Ph— |
| 111 | R1 and R2 are tert-butyl, R3 and R4 are H, R5 is —$(CH_2)_2$—O—Ph— |
| 112 (D3) | R1 and R2 are benzyl, R3 and R4 are H, R5 is —$(CH_2)_3$— |
| 113 | R1 and R2 are benzyl, R3 and R4 are H, R5 is —$CHBr(CH_2)_2$— |
| 114 | R1 and R2 are benzyl, R3 and R4 are H, R5 is —$CHPh(CH_2)_2$— |
| 115 | R1 and R2 are benzyl, R3 and R4 are H, R5 is —$CHCNCH_2$— |
| 116 | R1 and R2 are benzyl, R3 and R4 are H, R5 is —$CHBrCH_2$— |
| 117 (D4) | R1 is benzyl, R2 is n-butyl, R3 and R4 are H, R5 is —$(CH_2)_2$— |
| 118 | R1 is benzyl, R2 is n-butyl, R3 and R4 are H, R5 is —$(CH_2)_3$— |
| 119 | R1 is benzyl, R2 is n-butyl, R3 and R4 are H, R5 is —$(CH_2)_2$—O—Ph— |
| 120 | R1 is benzyl, R2 is n-butyl, R3 and R4 are H, R5 is —$(CH_2)_2$—O—Ph—, the para posistion of the phenyl ring is substituted by nitro. |

When preparing the compounds in Table 1, the solid reagents employed in the synthesis process are used directly without further treatment, the liquid reagents are used after redistilled and dried.

Example 1: Synthesis of Cytidine Derivative Dimer D1

The exemplary cytidine derivative dimer D1 can be 1,5-di-[4-N-(n-butyloxycarbonyl)-3'-O-(n-butoxycarbonyl)-2'-deoxy-2',2'-difluoro-cytidine]glutarate (also see No. 101 in Table 1) with the following structural formula:

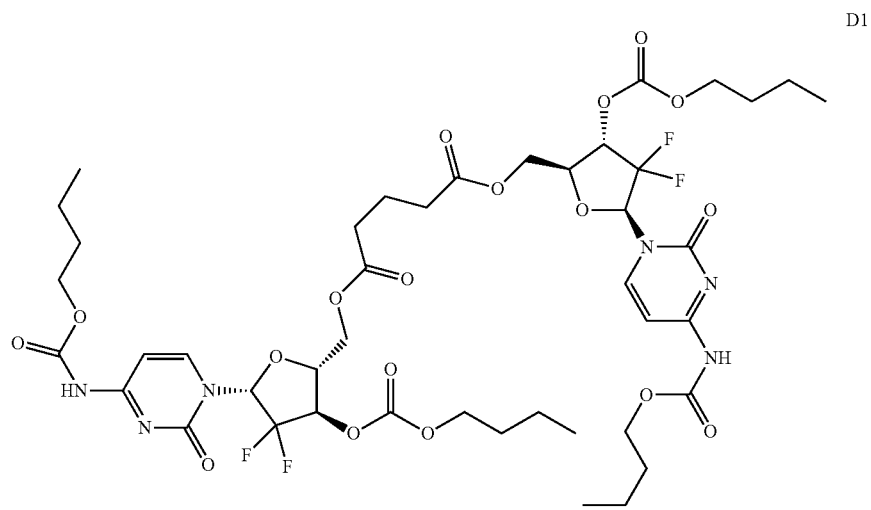 [SMILES: CCCCOC(=O)Nc1ccn([C@H]2O[C@@H](COC(=O)CCCC(=O)OC[C@H]3O[C@@H](n4ccc(NC(=O)OCCCC)nc4=O)C(F)(F)[C@@H]3OC(=O)OCCCC)[C@H](OC(=O)OCCCC)C2(F)F)c(=O)n1]

D1

Figure 2:
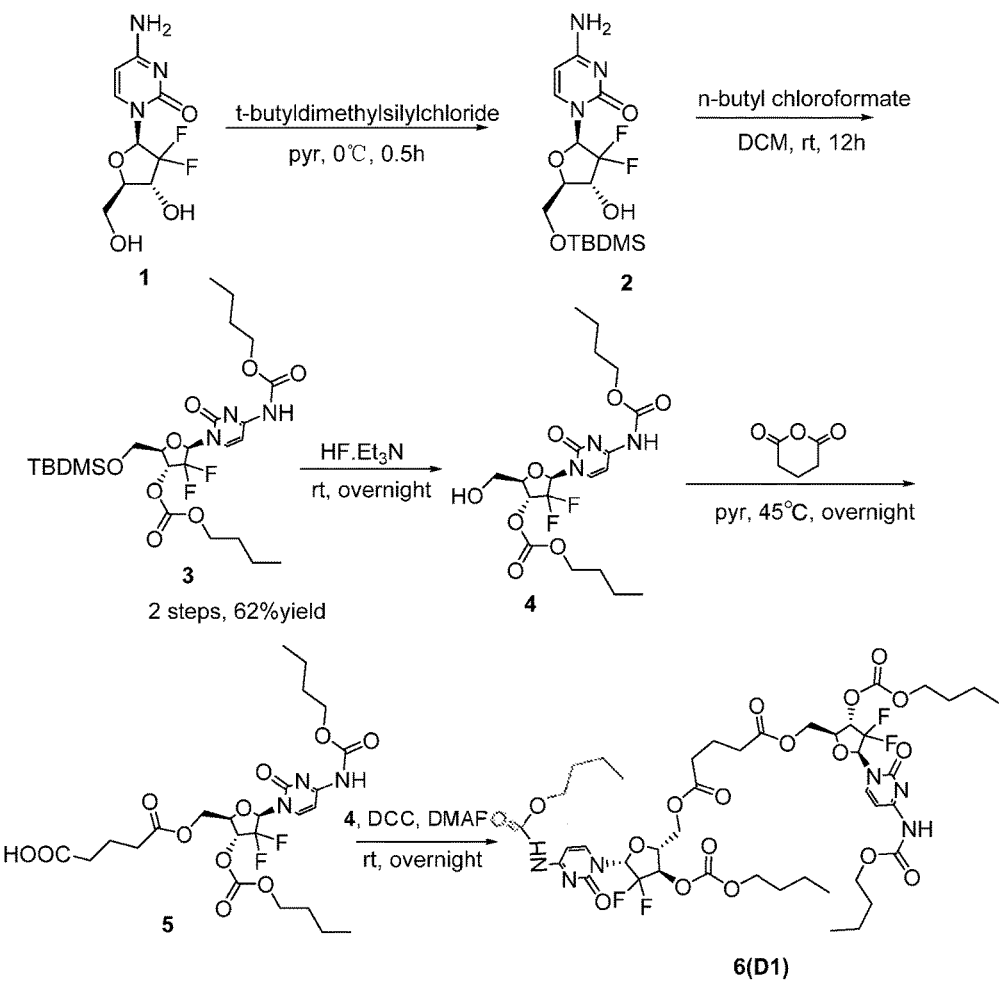
FIG. 2 illustrates an exemplary synthetic route of a cytidine derivative dimer in Example 1 consistent with various disclosed embodiments.

FIG. 2 illustrates an exemplary synthetic route of D1.

In an exemplary preparation of D1, 2'-deoxy-2', 2'-difluoro-cytidine hydrochloride (e.g., about 3 g, 10 mmol) and imidazole (e.g., about 0.875 g, 12.8 mmol) in anhydrous pyridine (e.g., about 10 mL) at 0° C. were added tert-butyldimethylsilyl chloride (TBSCL) (e.g., about 3.3 g, 21 mmol). The mixture was stirred for half an hour and warmed to room temperature, and the stirring was continued at room temperature for about 12 hours. The mixture was treated with methanol (e.g., about 8.0 mL). After stirring for about 60 minutes, the solvent was removed under reduced pressure. Compound 2 shown in FIG. 2 is then obtained in the reaction system.

Dichloromethane (DCM) (e.g., about 50 mL) and pyridine (e.g., about 10 mL) were then added into the reaction system, followed by adding Butyl chloroformate (e.g., about 5.46 g, 40 mmol) therein using an ice bath under nitrogen protection. Such solution was then stirred for about 12 hours at room temperature and all volatiles were removed using a rotary evaporator, leaving settled solid. The settled solid was dissolved in ethyl acetate (e.g., about 100 mL) and washed by cooled saturated sodium bicarbonate solution (e.g., about 30 mL for two times) and brine (e.g., about 30 mL). The resulting solution was dried over anhydrous sodium sulfate for about 3 hours and then filtered. The filtrate was purified by column chromatography (e.g., dichloromethane/methanol 40:1) to obtain intermediate Compound 3 (e.g., about 3.6 grams having a two-step yield of about 62%) as shown in FIG. 2.

Compound 3 (e.g., about 3.6 g, 6.23 mmol) was added into tetrahydrofuran (THF) (e.g., about 40 mL) and cooled in an ice bath to about 0° C. Triethylamine trihydrofluoride (e.g., about 4 mL) was slowly added. After 24 hours, the solvent was stripped to yield an orange solid, which was purified by column chromatography (dichloromethane/methanol, 20:1) to afford intermediate Compound 4 (e.g., about 1.68 g, with 58% yield).

The resulting intermediate Compound 4 (e.g., about 1.68 g, 3.62 mmol) was added chloroform (e.g., about 30 mL), followed by pyridine (e.g., about 30 mL) and glutaric anhydride (e.g., about 620 mg, 5.44 mmol) in the chloroform. The mixture was stirred at room temperature overnight. After that, 4-dimethylaminopyridine (DMAP, e.g., about 7 mg and 0.057 mmol) was then added and the mixture was stirred for about 3 hours. The reaction mixture was then concentrated to provide a viscous oily product, which was purified by column chromatography to obtain Compound 5 (e.g., about 1.11 g, with 53% yield).

Compound 5 (e.g., about 58 mg, 0.1 mmol), Compound 4 (e.g., about 92 mg, 0.2 mmol), and N,N'-Dicyclohexylcarbodiimide (DCC, e.g., about 42 mg, 0.2 mmol) were dissolved in dichloromethane (e.g., about 15 mL) and added DMAP (e.g., about 6 mg, 0.049 mmol). After stirring for about 24 hours at room temperature, dichloromethane (e.g., about 50 mL) was added. The mixture was then washed by water (e.g., about 10 mL), saturated brine (e.g., about 20 mL), dried over anhydrous sodium sulfate, and concentrated in vacuo. The resulting material was purified by column chromatography (dichloromethane/methanol, 20:1) to afford Compound 6 (e.g., about 49 mg, with 48% yield).

The structure of Compound 6 was verified by nuclear magnetic resonance (NMR) and mass spectroscopy (MS). $^1$H-NMR (MeOD-d4, 400 MHz) δ: 7.97 (d, 2H, J=7.68 Hz, H6-1, H6-2), 7.40 (d, 2H, J=7.68 Hz, H5-1, H5-2), 6.35 (t, 2H, J=7.24 Hz, H1'-1, H1'-2), 4.47 (m, 6H, H5a'-1, H5a'-2, H5b'-1, H5b'-2, H4'-1, H4'-2), 4.21 (m, 8H, O—CH2×4), 2.53 (t, 4H, J=7.16 Hz, CH2-CH2-CH2), 1.97 (m, 2H, CH2-CH2-CH2), 1.64 (m, 8H, O—CH2-CH2×4), 1.42 (m, 8H, O—CH2-CH2-CH2×4), 0.98 (m, 12H, CH2-CH3×4). $^{13}$C NMR (MeOD-d4, 100 MHz) δ: 172.83, 164.51, 153.87, 144.53, 96.26, 77.52, 69.13, 65.89, 61.94, 32.42, 30.66, 30.47, 18.83, 18.67, 12.79, 12.74, 8.48. ESIMS: calculated for C43H58F4N6O18 m/z 1023.37 (M+H)+, found 1023.66.

The synthetic route described in FIG. 2 can be adapted to produce various cytidine derivative dimers. For example, glutaric anhydride can be replaced with other anhydride(s) to produce corresponding compounds, such as compounds from No. 102 to No. 105 shown in Table 1. In another case, when tert-butyl chloroformate is used to replace butyl chloroformate, the produced compound can be compound No. 106 in Table 1.

Example 2: Synthesis of Cytidine Derivative Dimer D2

The exemplary cytidine derivative dimer can be 1,5-di-[4-N-(n-butoxycarbonyl)-2'-deoxy-2',2'-difluoro-cytidine] glutarate (also see No. 107 in Table 1) with following structural formula:

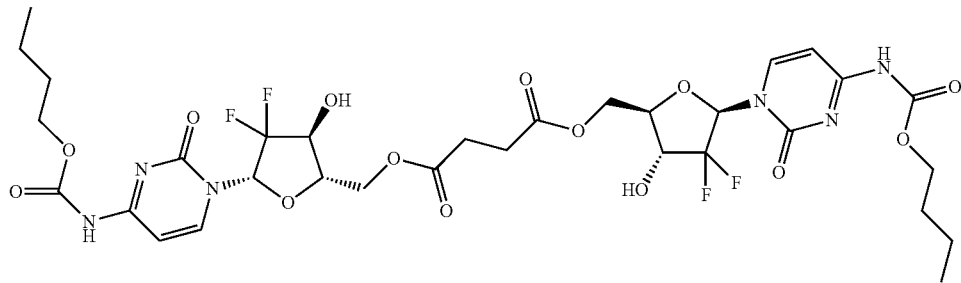

D2

Figure 3:
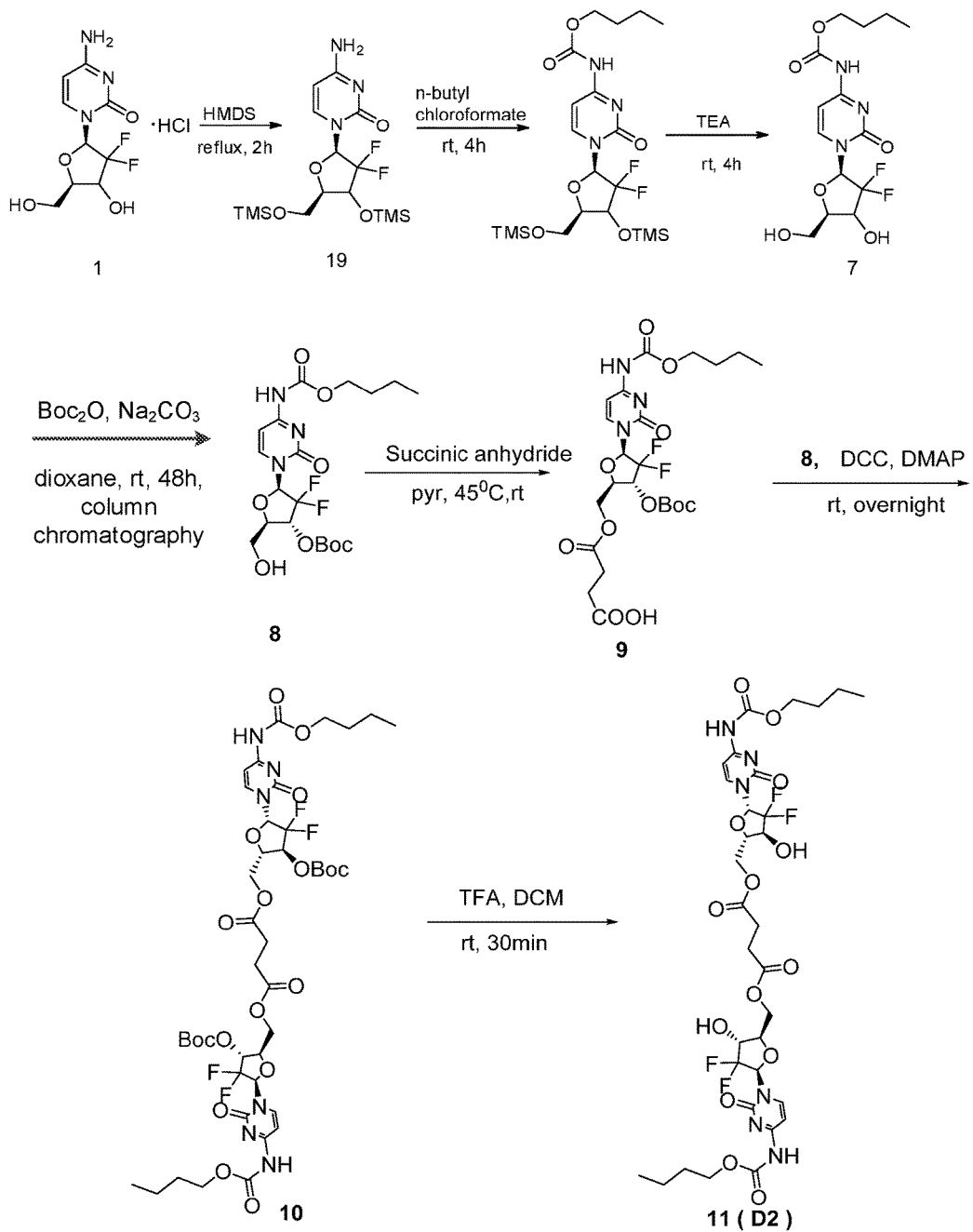
FIG. 3 illustrates an exemplary synthetic route of a cytidine derivative dimer in Example 2 consistent with various disclosed embodiments.

FIG. 3 illustrates an exemplary reaction process. As shown in FIG. 2, an intermediate Compound 8 was prepared first. In an exemplary preparation, 2'-deoxy-2', 2'-difluorocytidine hydrochloride (Compound 1 shown in FIG. 3, e.g., about 300 mg, 1 mmol), Bis(trimethylsilyl)amine (HMDS) (e.g., about 5 mL, 0.023 mmol), and ammonium sulfate (e.g. about 5 mg, as catalytic) were dissolved in 1,4-dioxane (e.g., about 5 mL). The reaction was heated under reflux for about 2 hours. Compound 19 shown in FIG. 3 was then obtained from the reaction. When the reflux reaction was completed, the reaction mixture was concentrated and azeotroped with toluene twice. The resulting dried solid was dissolved in dichloromethane (e.g., about 10 mL).

N-methylimidazole (e.g. about 0.24 mL, 3 mmol) and butyl chloroformate (e.g. about 0.32 mL, 3 mmol) were added into the dichloromethane solution and the mixture was stirred at room temperature for about 4 hours. The mixture was then concentrated to provide a viscous oily product.

The viscous oily product was dissolved in a mixed solution of triethylamine (e.g., about 3 mL) and methanol (e.g., about 20 mL), and stirred for about 4 hours at room temperature. Then, the solvent was removed under reduced pressure and the crude product was purified solved by silica gel column chromatography with dichloromethane/methanol (e.g., about 20:1) to afford Compound 7 (e.g., about 230 mg having a three-step yield of about 55.5%).

The structure of Compound 7 was verified by NMR: $^1$H-NMR (MeOD-$d_4$, 400 MHz) δ: 8.30 (d, 1H, J=7.68 Hz, H6), 7.34 (d, 1H, J=7.68 Hz, H5), 6.28 (t, 1H, J=7.08 Hz, H1'), 4.33 (m, 1H, H5a'), 4.0 (m, 2H, O—CH$_2$—CH$_2$—), 3.81 (m, 1H, H5b'), 3.79 (m, 1H, H4'), 1.68 (m, 2H, O—CH$_2$—CH$_2$—), 1.45 (m, 2H, O—CH$_2$—CH$_2$—CH$_2$), 0.98 (t, 3H, J=7.4 Hz, —CH$_2$—CH$_3$). $^{13}$C-NMR (MeOD-$d_4$, 100 MHz) δ 164.28, 156.27, 153.50, 144.39, 128.33, 122.72, 95.81, 84.90, 81.71, 74.87, 68.88, 63.69, 59.15, 30.66, 32.40, 18.81, 11.23, 8.06.

Compound 7 (e.g. about 60 mg, 0.16 mmol) and sodium carbonate (e.g. about 106 mg, 1 mmol) were dissolved in a solution of 1,4-dioxane and water (e.g., about 5 mL, volume ratio about 4:1). Di-tert-butyl dicarbonate (Boc)$_2$O (e.g., about 44 mg, 0.2 mmol) was added and the mixture was stirred at room temperature for about 48 hours. The reaction mixture was diluted with water (e.g., about 2 mL) and extracted with ethyl acetate twice (e.g., about 30 mL×2). The combined organic phase was washed by water (e.g., about 5 mL), saturated saline (e.g., about 5 mL), dried over anhydrous sodium sulfate, and then concentrated under reduced pressure. The resulting dried solid was purified by silica gel column chromatography with dichloromethane/acetone/methanol (e.g., about 1:1:0.02) to afford Compound 8 (e.g., about 51 mg, with 76% yield).

Referring back to FIG. 3, in an exemplary preparation of D2, to a solution of Compound 8 (e.g., about 223 mg, 0.25 mmol) in chloroform (e.g., about 6 mL) was added pyridine (e.g., about 5 mL) and butanedioic anhydride (e.g., about 100 mg, 1 mmol). The mixture was stirred at about 45° C. overnight. Then the reaction mixture was concentrated to viscous oil and purified by column chromatography (e.g., DCM-MeOH about 20:1 to 10:1) to afford Compound 9 (e.g. about 211 mg, with 75% yield).

Compound 9 (e.g., about 56 mg, 0.1 mmol), Compound 8 (e.g., about 92 mg, 0.2 mmol) and DCC (e.g., about 42 mg, 0.2 mmol), were dissolved in dichloromethane (e.g., about 15 mL) and DMAP (e.g., about 6 mg, 0.049 mmol) was added. After stirring at room temperature for about 24 hours, the reaction mixture was diluted with dichloromethane (e.g., about 50 mL) and washed with water (e.g., about 10 mL), saturated brine (e.g., about 20 mL), dried over anhydrous sodium sulfate, and concentrated. The resulting material was added trifluoroacetic acid (TFA) (e.g., about 5 mL) and DCM (e.g., about 10 mL) and stirred at room temperature for about half an hour. The reaction mixture was cooled to 0° C. and filtered to remove any precipitate. The filtrate was concentrated and purified by column chromatography (e.g., DCM-MeOH about 20:1 to 10:1) to afford the cytidine derivative dimer D2 (e.g., about 30 mg, with 35% yield).

The structure of D2 was verified by NMR and MS: $^1$H-NMR (MeOD-$d_4$, 400 MHz) δ 7.85 (d, 2H, J=7.68 Hz, H6-1, H6-2), 7.37 (d, 2H, J=7.68 Hz, H5-1, H5-2), 6.26 (t, 2H, J=7.24 Hz, H1'-1, H1'-2), 4.53 (m, 2H, H5a'-1, H5a'-2), 4.40 (m, 4H, H5b'-1, H5b'-2, H4'-1, H4'-2), 4.20 (m, 2H, H3-1, H3-2), 2.73 (m, 4H, —CH2-CH2-), 1.64 (m, 4H, O—CH2-CH2), 1.37 (m, 4H, O—CH2-CH2-CH2), 0.93 (m, 6H, CH2-CH3). $^{13}$C-NMR (MeOD-$d_4$, 100 MHz) δ 172.41, 164.01, 155.95, 153.52, 144.36, 96.56, 70.53, 66.29, 62.49, 30.74, 28.76, 19.01, 13.49. ESIMS: calculated for $C_{32}H_{40}F_4N_6O_{14}$ m/z 809.25 (M+H)$^+$, found 809.34.

The exemplary preparation described in FIG. 3 can be adapted to produce various cytidine derivative dimers. For example, Compound 8 can react with other dianhydride(s), such as glutaric anhydride, to produce corresponding compounds, such as compounds from No. 108 to No. 110 shown in Table 1. In another case, when tert-butyl chloroformate is used to replace butyl chloroformate, the produced compound can be compound No. 111 shown in Table 1.

Example 3: Synthesis of Cytidine Derivative Dimer D3

The exemplary cytidine derivative dimer D3 can be 1,5-di-[4-N-(benzyloxycarbonyl)-2'-deoxy-2',2'-difluorocytidine]glutarate (also see No. 112 in Table 1).

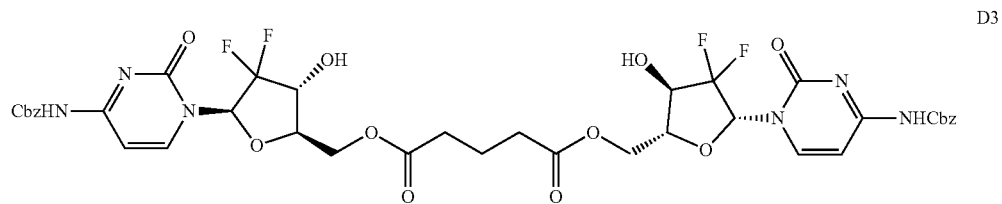 [SMILES: O=C(CCCC(=O)OC[C@H]1O[C@@H](n2ccc(NC(=O)OCc3ccccc3)nc2=O)C(F)(F)[C@@H]1O)OC[C@H]1O[C@@H](n2ccc(NC(=O)OCc3ccccc3)nc2=O)C(F)(F)[C@@H]1O]

Figure 4:
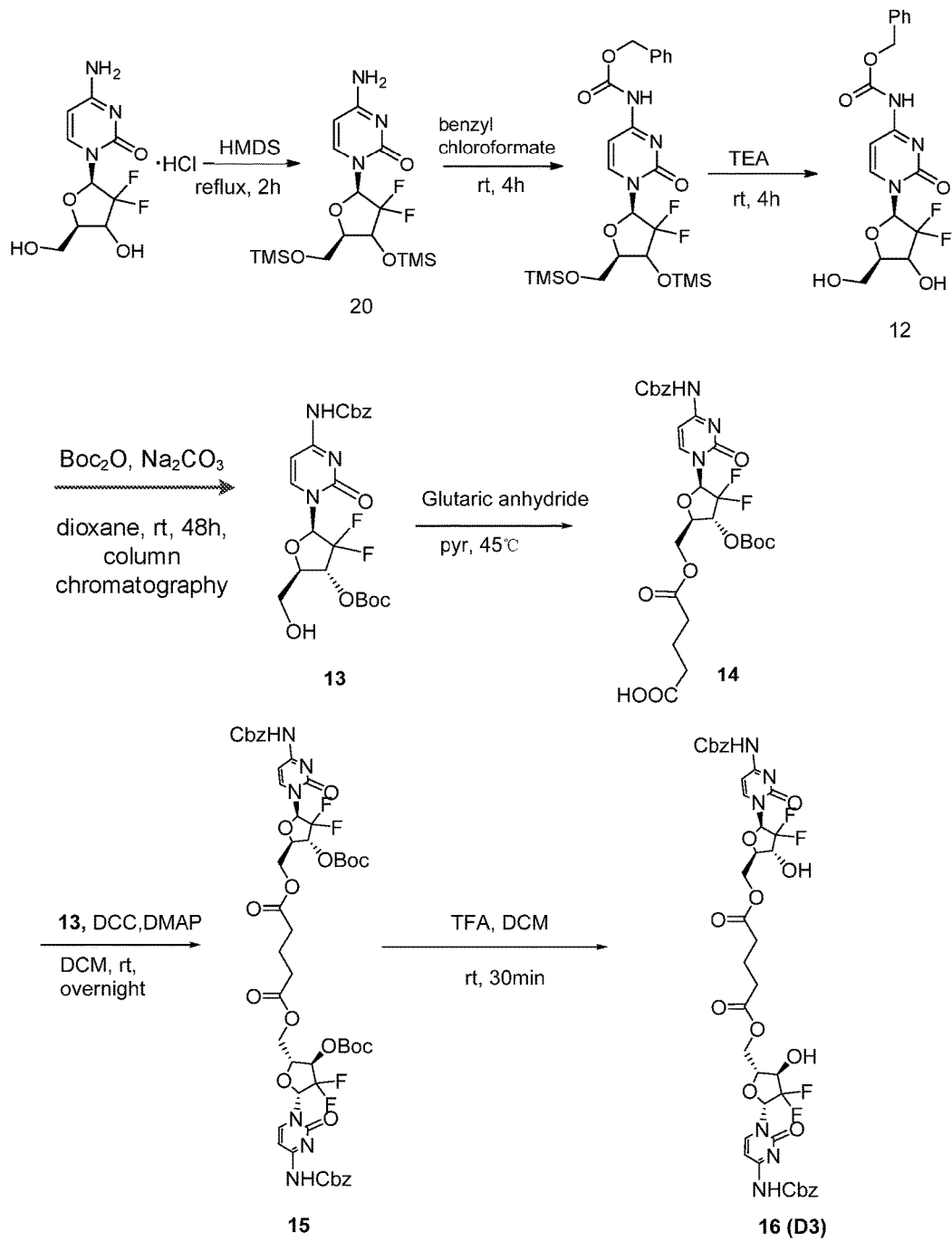
FIG. 4 illustrates an exemplary synthetic route of a cytidine derivative dimer in Example 3 consistent with various disclosed embodiments.

FIG. 4 illustrates an exemplary synthetic route of D3.

In an exemplary preparation, Compound 13 was prepared first as follows. 2'-deoxy-2', 2'-difluoro-cytidine hydrochloride (e.g., about 300 mg, 1 mmol), Bis(trimethylsilyl)amine (e.g., about 5 mL, 0.023 mmol), and ammonium sulfate (e.g., about 5 mg as catalytic) were dissolved in 1,4-dioxane (e.g., about 5 mL). The reaction was heated under reflux for about 2 hours. After that, the reaction mixture was concentrated and azeotroped with toluene twice. The resulting solid was dissolved in dichloromethane (e.g., about 10 mL).

N-methylimidazole (e.g. about 0.24 mL, 3 mmol) and benzyl chloroformate (e.g., about 340 mg, 3 mmol) were added to the dichloromethane solution. After stirring at room temperature for about 4 hours, Compound 20 as shown in FIG. 4 was obtained. The reaction mixture was then concentrated to provide a viscous oily product.

The viscous oily product was dissolved in a mixed solution of triethylamine (e.g., about 3 mL) and methanol (e.g., about 20 mL), and stirred at room temperature overnight. The solvent was then removed by distilling under reduced pressure. The crude product was purified by silica gel column chromatography with dichloromethane/methanol (e.g., about 20:1) to afford Compound 12 (e.g., about 162 mg, three-step yield of about 41%).

The NMR characterizations of Compound 12 include: $^1$H-NMR (MeOD-$d_4$, 400 MHz) δ: 8.31 (d, 1H, J=7.64 Hz, H6), 7.39 (m, 5H, J=7.68 Hz, Ph), 6.25 (t, 1H, J=7.12 Hz, H1'), 5.21 (s, 2H. CH$_2$-Ph), 4.31 (m, 1H, H5a'), 3.82 (m, 2H, H5b, H4'), 3.79 (m, 1H, H3'). $^{13}$C-NMR (MeOD-$d_4$, 100 MHz) δ: 164.22, 156.22, 153.27, 144.48, 135.87, 128.42, 128.10, 125.31, 122.74, 120.16, 95.89, 85.35, 84.91, 81.7, 81.66, 68.87, 67.54, 58.31.

Compound 12 (e.g., about 80 mg, 0.2 mmol) and sodium carbonate (e.g., about 106 mg, 1 mmol) were dissolved in a solution of 1,4-dioxane and water (e.g., about 5 mL, volume ratio about 4:1). Then (Boc)$_2$O (e.g., about 44 mg, 0.2 mmol) was added and the mixture was stirred for about 48 hours at room temperature. After that, the reaction mixture was diluted with water (e.g., about 2 mL) and extracted with ethyl acetate twice (e.g., about 30 mL X$_2$). The combined organic extract was washed with water (e.g., about 5 mL), saturated saline (e.g., about 5 mL), dried over anhydrous sodium sulfate, and concentrated. The remaining residue was then purified by column chromatography (dichloromethane/acetone/ethanol, about 1:1:0.02) to afford Compound 13 (e.g., about 64 mg, with 64% yield).

To a solution of Compound 13 (e.g., about 248 mg, 0.5 mmol) in chloroform (e.g., about 15 mL) was added pyridine (e.g., about 5 mL), and glutaric anhydride (e.g., about 100 mg, 1 mmol), After stirring at about 45° C. overnight, the reaction mixture was concentrated to viscous oil, followed by purification with column chromatography (DCM-MeOH 20:1 to 10:1) to afford Compound 14 (e.g., about 223 mg, with 73% yield).

Compound 14 (e.g., about 61 mg, 0.1 mmol), Compound 13 (e.g., about 99 mg, 0.2 mmol) and DCC (e.g., about 42 mg, 0.2 mmol) were dissolved in dichloromethane (e.g., about 15 mL), and DMAP (e.g., about 6 mg, 0.049 mmol) was added. After stirring at room temperature for about 24 hours, the reaction mixture was diluted with dichloromethane (e.g., about 50 mL) and washed with water (e.g., about 10 mL), saturated brine (e.g., about 20 mL), dried over anhydrous sodium sulfate, and concentrated. The remaining residue was treated with TFA (e.g., about 5 mL) and DCM (e.g., about 10 mL), followed by stirring at room temperature for about half an hour. After that, the reaction mixture was cooled in an ice-bath, and the resulting precipitate was removed by filtration. The filtrate was then concentrated to provide a viscous oil, which was purified by column chromatography (DCM-MeOH about 20:1 to 10:1) to afford D3 (e.g., about 30 mg, with 35% yield).

The characterizations of D3 include: $^1$H-NMR (MeOD-$d_4$, 400 MHz) δ: 8.31 (d, 1H, J=7.64 Hz, H6), 7.39 (m, 5H, J=7.68 Hz, Ph), 6.27 (t, 2H, J=7.8 Hz, H1'-1, H1'-2), 5.17 (s, 4H, CH$_2$-Ph×2), 4.46 (m, 4H, H5a'-1, H5a'-2, H5b'-1, H5b'-2), 4.21 (m, 2H, H4'-1, H4'-2), 4.10 (m, 2H, H3'-1, H3'-2), 2.53 (t, 4H, J=7.16 Hz, —CH2-CH2-CH2-), 1.99 (q, 2H, J=7.2 Hz, —CH2-CH2-CH2-). $^{13}$C NMR (MeOD-$d_4$, 100 MHz) δ 172.90, 164.21, 155.90, 153.31, 144.25, 141.03, 135.86, 128.41, 128.28, 128.10, 124.85, 123.25, 122.26, 96.14, 79.17, 74.97, 67.59, 62.06, 33.19, 32.51, 19.96. ESIMS: calculated for C$_{39}$H$_{38}$F$_4$N$_6$O$_{14}$ m/z 891.24 (M+H)$^+$, found 891.31.

The exemplary preparation described in FIG. 4 can be adapted to produce various cytidine derivative dimers. For example, Compound 14 can react with other dianhydride(s), such as COOHCHBr(CH$_2$)$_2$COOH, COOH CHPh(CH$_2$)$_2$ COOH, and COOH CHCNCH$_2$COOH, to produce corresponding compounds, such as compounds from No. 113 to No. 116 shown in Table 1.

Example 4: Synthesis of Cytidine Derivative Dimer D4

The exemplary cytidine derivative dimer D4 can be 1-O-(4-N-(Benzyloxycarbonyl)-gemcitabine)-4-O-(4-N-(n-Butoxycarbonyl)-gemcitabine)-succinate (also see No. 117 in Table 1) with the following structural formula:

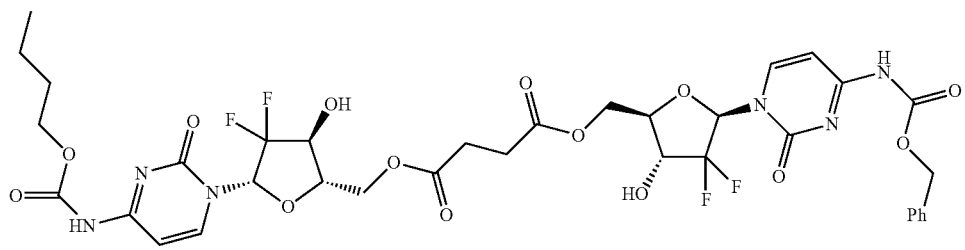

D4

Figure 5:
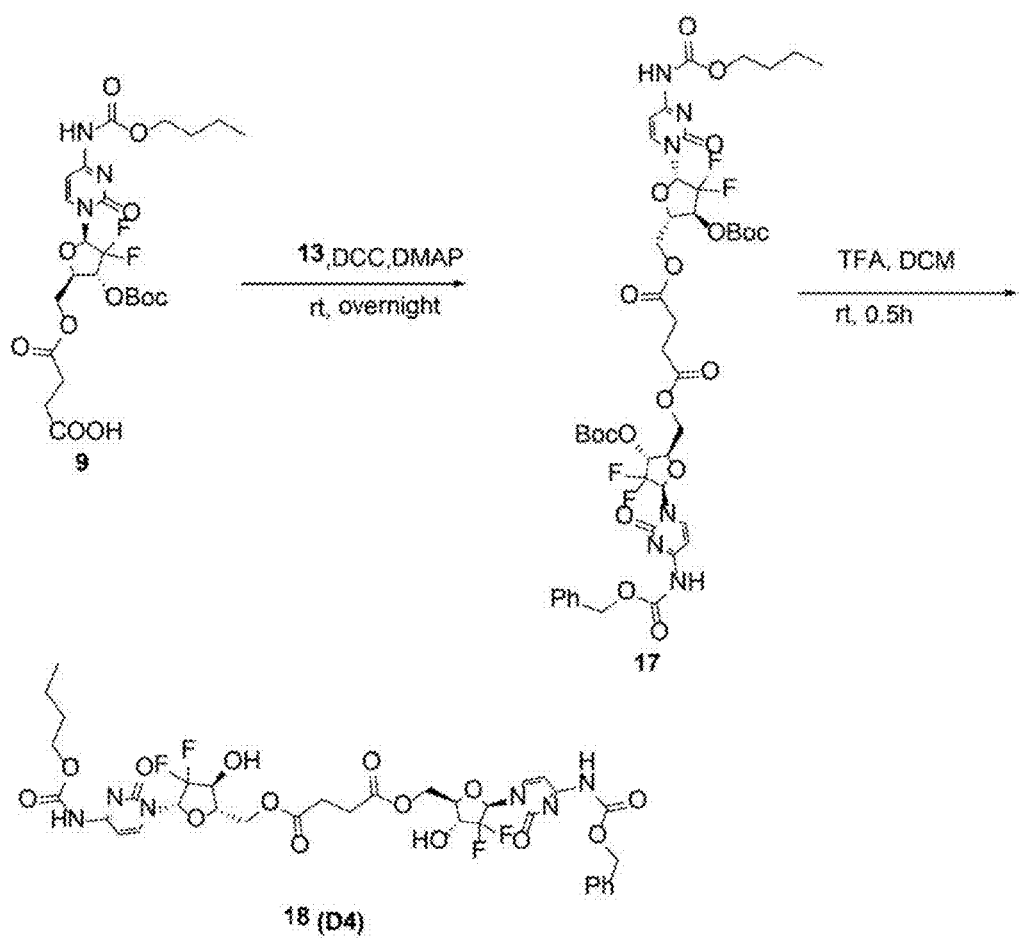
FIG. 5 illustrates an exemplary synthetic route of a cytidine derivative dimer in Example 4 consistent with various disclosed embodiments.

FIG. 5 illustrates an exemplary synthetic route of D4.

In an exemplary preparation, Compound 9 (e.g., about 56 mg, 0.1 mmol), Compound 13 (e.g., about 99 mg, 0.2 mmol) and DCC (e.g., about 42 mg, 0.2 mmol) were dissolved in dichloromethane (e.g., about 15 mL), and DMAP (e.g., about 6 mg, 0.049 mmol) was added. After stirring at room temperature for about 24 hours, the reaction mixture was diluted with dichloromethane (e.g., about 50 mL) and washed with water (e.g., about 10 mL), saturated brine (e.g., about 20 mL), dried over anhydrous sodium sulfate, and concentrated. The remaining residue was treated with TFA (e.g., about 5 mL) and DCM (e.g., about 10 mL) for about half an hour at room temperature. After that, the reaction mixture was cooled in an ice-bath and the resulting precipitate was removed by filtration. The filtrate was concentrated to provide a viscous oil and purified by column chromatography (DCM-MeOH about 20:1 to 10:1) to afford D4 (e.g., about 30 mg, 36% yield).

The characterizations of D4 include: $^1$H-NMR (MeOD-d$_4$, 400 MHz) δ 7.98 (m, 2H, H6-1, H6-2), 7.40 (d, 2H, J=7.68 Hz, H5-1, H5-2), 7.38 (m, 6H, Ph), 6.26 (t, 2H, J=8 Hz, H1'-1, H1'-2), 5.21 (s, 2H, CH$_2$-Ph), 4.43 (m, 2H, H5a'-1, H5a'-2), 4.29 (m, 2H, H5b'-1, H5b'-2), 4.21 (m, 6H, H4'-1, H4'-2H3'-1, H3'-2), 2.74 (m, 4H, —CH$_2$—CH$_2$—), 1.43 (m, 2H, O—CH$_2$—CH$_2$—), 1.28 (m, 2H, O—CH$_2$—CH$_2$—CH$_2$—), 0.97 (t, 3H, J=7.4 Hz, —CH$_2$—CH$_3$). $^{13}$C NMR (MeOD-d$_4$, 100 MHz) δ 172.56, 164.19, 155.89, 153.52, 144.61, 135.86, 128.09, 122.22, 96.21, 79.38, 78.91, 70.83, 67.60, 65.92, 62.11, 56.72, 30.64, 28.66, 28.51, 25.93, 18.82, 14.26, 12.77. ESIMS: calculated for C$_{35}$H$_{38}$F$_4$N$_6$O$_{14}$ m/z 843.24 (M+H)$^+$, found 843.33.

The exemplary preparation described in FIG. 5 can be adapted to produce various cytidine derivative dimers. For example, butanedioic anhydride can be replaced with other anhydride(s) to react with Compound 8 and produce an intermediate compound. The intermediate compound can then react with Compound 13 to produce corresponding compounds, such as compounds from No. 118 to No. 120 shown in Table 1.

Example 5: Preparation of Cytidine Derivative Dimer Hydrochloride

In an exemplary preparation of hydrochloride of the exemplary cytidine derivative dimer in Example 1 including exemplary cytidine derivative dimer D1, 1,5-di-[4-N-(n-butyloxycarbonyl)-3'-O-(n-butoxycarbonyl)-2'-deoxy-2',2'-difluoro-cytidine]glutarate (e.g., about 0.50 g) was dissolved in ethyl acetate (e.g., about 60 mL). The solution was cooled in an ice bath and treated with dry hydrochloric acid gas. After stirring for 15 minutes, the solvent was removed to obtain the HCl salt of the product as white solid.

Similar procedure can be used to prepare other hydrochloride of the disclosed cytidine derivative dimer(s).

In addition to hydrochloride salt disclosed herein, other cytidine derivative dimer-based salts including phosphates, sulfates, carbonates, nitrates, citrates, tartrates, maleates, succinates, sulfonates, p-toluenesulfonates, methanesulfonates, benzoates or fumarates of the disclosed cytidine derivative dimer can also be prepared accordingly.

The present disclosure also relates to treatment of cancer. More specifically, various embodiments may be directed to the treatment of a subject, particularly a mammal such as a human, having a neoplasm by administering a therapeutically effective amount of a novel compound of formula (I) to the subject for a period of time sufficient to produce an anti-neoplastic result.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. Various types of cancers, i.e., malignant tumors or neoplasia may be treated by administering the disclosed compound.

The disclosed compounds can be useful in the treatment of a neoplasm, e.g. leukemia and solid tumors, such as colon, colo-rectal, ovarian, mammary, prostate, lung, kidney and melanoma tumors. The dosage range adopted may depend on the route of administration and on the age, weight and condition of the patient being treated. The compounds may be administered, for example, by the parenteral route, for example, intramuscularly, intravenously or by bolus infusion.

As used herein, a patient or subject is a vertebrate having cancer or other diseases. Preferably, the subject is a warm-blooded animal, particularly a mammal which includes both human and non-human mammals. Examples of non-human mammals include but are not limited to farm animals, such as cows, sheep, pigs, goats, horses, and llama, and pets, such as dogs and cats. More preferably, the subject is a human. The compounds are shown herein as Formula I and are described in more detail hereinafter. A therapeutically effective amount of the compound is administered to a subject in need thereof for a period of time sufficient to obtain an antineoplastic effect.

With mammals, including humans, the effective amounts can be administered on the basis of body surface area. A suitable dose range may be from 1 mg to 1000 mg of equivalent disclosed compound per m$^2$ body surface area, for instance from 50 mg/m$^2$ to 500 mg/m$^2$.

Example 6: Lyophilized Powder of Cytidine Derivative Dimer for Injection

In an exemplary preparation of injectable lyophilized powder of compound D3 in Example 3, the injectable lyophilized powder of D3 may include compound D3 (e.g. about 30 g), mannitol (e.g., 20% w/v, about 300 g), buffer sodium dihydrogen phosphate dihydrate (e.g., about 7 g), and surfactant poloxamer 188 (F68) (e.g., about 4.0 g).

The sodium dihydrogen phosphate dihydrate, the poloxamer 188 (F68) (CAS No.: 9003-11-6), and the mannitol (e.g., about 20% w/v) were weighed according to the prescription amount as suggested above, and then dissolved in water (e.g., about 300 g) for injection which was pre-cooled to a temperature lower than about 10° C. NaOH (0.1 mol/L) was used to adjust the pH value of the solution to about 7.3-7.5. Prescribed dosage of D3 was then added to the solution and homogeneously mixed. NaOH solution (0.1 mol/L) or HCl (0.1 mol/L) can be used to adjust the pH value to about 7.3±0.2 (about 7.5 in this Example). The solution was added with water until 2000 g, and then sterilized by 0.22 μm microfiltration. The filtrate was dispensed in vials for about 2.0 grams in each vial. The vials were partially stoppered, and placed in a freeze dryer for lyophilization. After drying, the vials were vacuum packed, capped, and labeled to prepare about 1000 vials of lyophilized powder injections. The storage temperature was about 2° C.-8° C.

In addition to the injectable lyophilized powder (i.e., sterile powder for injection), the cytidine derivative dimer(s) in present disclosure may be formulated in any other suitable forms for injection, such as a solution-type injection, a suspension-type injection, an emulsion-type injection, liposomal injection, and/or a sterile powder-type for injection.

Example 7: Pharmaceutical Composition of Cytidine Derivative Dimer(s)

An exemplary pharmaceutical composition of cytidine derivative dimer may include pharmaceutically active ingredients and excipients. The pharmaceutically active ingredient may include the disclosed cytidine derivative dimer or corresponding salt thereof. The weight percentage of the active ingredient in the pharmaceutical composition can be about 1% to about 95% (about 30% in this Example). The excipients may include water, lactose, corn starch, hydroxypropylmethyl cellulose and magnesium stearate. The pharmaceutical compositions can be in various forms including, for example, a tablet.

In addition to the tablet form, the pharmaceutical composition can take other suitable forms. The pharmaceutically active ingredient can be prepared for oral administration in a form as: powders, granules, capsules, pellets formulations, solutions, suspensions, emulsions, syrups or elixirs, or slow-controlled release formulation and controlled release formulations, or other suitable forms for oral administration. These orally administered types of pharmaceutical composition may contain commonly used excipients (including, e.g., additives, appendages, etc. depending on their functions) corresponding to the pharmaceutical composition. The additives may include mannitol, lactose, starch, magnesium stearate, sugar, salt, cellulose, magnesium sulfate, etc. in pharmaceutical grades.

When preparing the exemplary orally administered type of pharmaceutical composition, appendages in pharmaceutical grade may be used as medicinal carriers for carrying the pharmaceutically active ingredients and include, for example: inert solid diluents, aqueous solvents, liposomes, microspheres and/or non-toxic organic solvents. Any suitable appendages in pharmaceutical grade can be used herein. In one embodiment, the appendages in pharmaceutical grade may include: wetting agents, emulsifying agents, pH buffers, human serum albumin, antioxidants, preservatives, bacteriostatic agents, dextrose, sucrose, trehalose, maltose, lecithin, glycine, sorbic acid, propylene glycol, polyethylene, protamine, boric acid, sodium chloride, potassium chloride, mineral oil, vegetable oil, or a combination thereof.

The target tumors of the disclosed pharmaceutical composition may include blood tumors (e.g., neoplastic hematologic disorder) or malignant solid tumors. Specifically, target tumors may include lung cancer, prostate cancer, breast cancer, colon cancer, stomach cancer, pancreatic cancer, liver cancer, esophageal cancer, brain tumor, ovarian cancer, uterine cancer, kidney cancer, head and neck cancer, skin cancer, bladder cancer, vulvar cancer, testicular tumor, colorectal cancer, choriocarcinoma, germ cell tumors, malignant lymphoma, leukemia and multiple myeloma. Further, an exemplary target tumor may include pancreatic cancer (in a first-line or second-line treatment), non-small cell lung cancer, small cell lung cancer, breast cancer, ovarian cancer and head and neck squamous cell carcinoma, and/or colon cancer. However, target tumors that may be treated by the disclosed pharmaceutical composition are not limited thereto.

Application Example 1: Inhibition Test of a Series of Compounds on HCT-116 Human Colon Cancer Cell Colony Formation 1. The colony formation inhibition test was used to evaluate the effect of four exemplary candidate compounds (D1, D2, D3, and D4) having concentrations of 50 nM, 150 nM and 450 nM on inhibiting cell proliferation of HCT-116 human colon cancer cells line.

2. Experiment material includes cell lines. HCT-116 human colon cancer cell line was purchased from the Chinese Academy of Sciences Shanghai Cell Resource Center, Cat # TCHu 99.

3. Reagent preparation includes HCT-116 human colon cancer cell culture medium, e.g., Dulbecco's Modified Eagle's medium (DMEM) medium with 10% fetal bovine serum (FBS). Compound solutions were prepared by dissolving and diluting the above synthesized compounds in dimethyl sulfoxide (DMSO) to a final concentration of about 100 μM.

Cell staining solution was prepared including 0.5% crystal violet solution prepared using absolute or anhydrous ethanol, and stored in dark. Before staining, the solution was mixed with phosphate buffered saline (PBS) buffer solution by volume ratio of 1:4 as the cell staining solution.

4. Cell culture: cells in logarithmic growth phase were collected, counted, and resuspended in complete culture medium. The cell concentration was adjusted to an appropriate concentration, 6-well culture plates were seeded, with about 300 cells and 1.8 mL of culture medium in each well. Cells were incubated for about 5 hours in an incubator at about 37° C. and about 100% relative humidity and under 5% $CO_2$.

5. Cell colony formation inhibition test and data processing were performed including, for example, (a)-(i) as follows.

(a) Cells in logarithmic growth phase were collected and counted. The cells were re-suspended in culture medium containing 5% FBS, and counted. Six-well plates were seeded according to a rate of 300 cells per well. Cells were incubated for about 5 hours in an incubator at about 37° C. with 100% relative humidity and under 5% $CO_2$.

(b) The compounds were diluted with culture medium (containing 5% FBS) to be concentrations of about 0.5 μM, 1.5 μM and 4.5 μM. Adding the compounds to cells in 200

µL per well, the final concentrations of the compounds were about 50 nM, 150 nM and 450 nM. Each concentration point was repeatedly tested for three times.

(c) Cells were incubated for about 72 hours in an incubator at 37° C. with 100% relative humidity and under 5% $CO_2$. (d) The culture medium from the plates (the culture medium containing the compound(s) was aspirated. The plates were rinsed with Hank's Balance Salt Solution (HBSS) twice, and replaced with fresh culture medium (DMEM medium with 15% FBS).

(e) Cells were incubated for about 7-10 days in an incubator at about 37° C. and 100% relative humidity and under 5% $CO_2$, until the formation of visible cloned plaques. (f) The culture medium was aspirated from the plates. The plates were rinsed twice with PBS solution. (g) The residual PBS was absorbed and removed, and ethanol was added at 1 mL per plate, fixing for 30 minutes.

(h) Ethanol was absorbed and removed, and cell staining solution was added, stained for 3 minutes. (i) The staining solution was aspirated. After rinsing three times with PBS, the cells were counted.

Data processing was performed. Cloning formation efficiency=[As/Ac]×100%; and colony formation inhibition rate=1−cloning formation efficiency, where As denotes number of cell colonies in compound-treated group (cells+ compounds to be tested), and Ac denotes number of cell colonies in negative control (without treating with compound) (cells+1% DMSO).

6. Results and discussion: Table 2 lists numbers of cell colonies of HCT-116 human colon cancer cells treated with the four compounds, where % inhibition means inhibition rate.

TABLE 2

Numbers of cell colonies of HCT-116 human colon cancer cells treated with the four compounds.
Number of cell clones on HCT-116

| | DG-1 | | DG-2 | | DG-3 | | DG-4 | |
|---|---|---|---|---|---|---|---|---|
| | mean | % inhibition | mean | % inhibition | mean | % inhibition | mean | % inhibition |
| Control | 251 | | 255 | | 241 | | 256 | |
| 50 nM | 242 | 3.58% | 243 | 4.70% | 237 | 1.66% | 235 | 8.20% |
| 150 nM | 188 | 25.10% | 191 | 25.10% | 20 | 91.70% | 75 | 70.70% |
| 450 nM | 52 | 79.28% | 36 | 85.88% | 4 | 98.34% | 11 | 95.70% |

Figure 6:
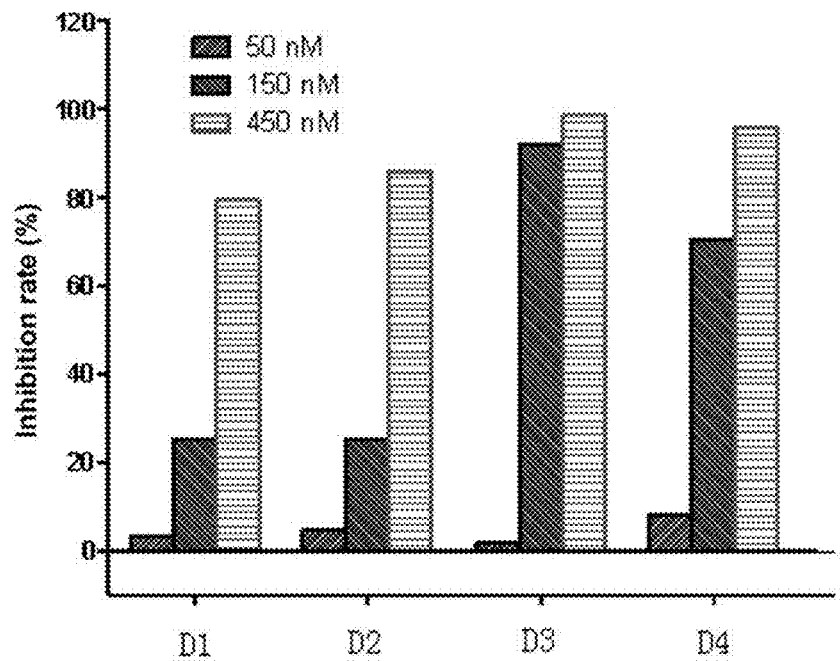
FIG. 6 is a bar chart illustrating cell colony formation inhibition rates of HCT-116 human colon cancer cells treated with four compounds at different concentrations consistent with various disclosed embodiments.

FIG. 6 is a bar chart illustrating the cell colony formation inhibition rates of HCT-116 human colon cancer cells treated with the four compounds at concentrations of about 50 nM, 150 nM and 450 nM. Table 2 and FIG. 6 show that the disclosed compounds have significant effects in inhibiting tumor cells.

Figure 7:
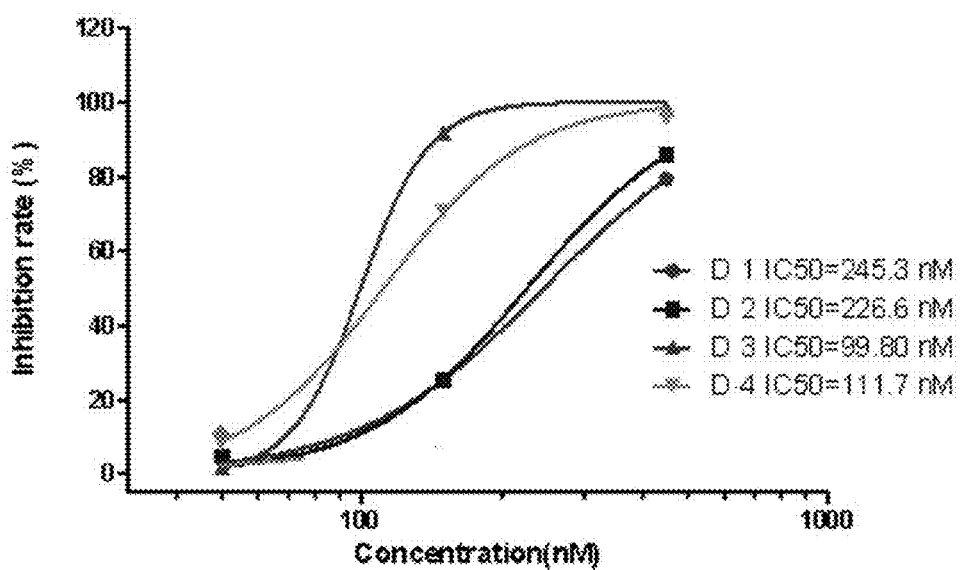
FIG. 7 is a curve chart illustrating a dose-response relationship between inhibition rates and compound concentrations after HCT-116 human colon cancer cells were treated with the four compounds consistent with various disclosed embodiments.

FIG. 7 is a curve chart illustrating the dose-response relationship between the inhibition rates and the compound concentrations when the four compounds reacting with the HCT-116 human colon cancer cells. As shown in FIG. 7, the IC50 value of D1 was about 245.3 nM, the IC50 value of D2 was about 226.6 nM, the IC50 value of D3 was about 99.80 nM, and the IC50 value of D4 was about 111.7 nM.

Application Example 2: Effects of a Series of Compounds on Tumor Growth Inhibition By observing the tumor formation and growth at inoculation sites and changes in body weight of test animals, this application example evaluated tumor growth inhibition of HCT-116 human colon cancer xenografts and toxicity of a single intraperitoneal injection of the compounds D1 to D4 in HCT-116 colon tumor-bearing nude mice.

1. Experiment objectives were to measure tumor growth inhibition of HCT-116 human colon cancer xenografts and to evaluate toxicity of a single intraperitoneal injection of the disclosed cytidine derivative dimer compounds to HCT-116 colon tumor-bearing nude mice.

2. Preparation of the test substance was performed by dissolving the test substance using the following solvents:

| Solvent | Lot number | Suppliers |
|---|---|---|
| Absolute ethanol | 10009218 | Sinopharm Chemical Reagent Co., Ltd (Shanghai, China) |
| Cremophor EL | 27963 | Sigma-Aldrich (Shanghai, China) |
| 0.9% saline | 13083004 | HUA YU Pharmaceutical Co., Ltd (Wuxi, China) |

Corresponding test substance was weighed and put into a 5 mL glass tube. The test substance was dissolved in ethanol under the stirring by a 5 mm magnetic stirrer. After a complete dissolution, Cremophor EL was added with continuous stirring. Immediately prior to the user of the test substance, the labeled amount of physiological saline was added and stirred. The ethanol, Cremophor EL, physiological saline had a volume ratio of 5:5:90 in a final solution.

3. Animal experiments were performed. The animals were female Balb/c nude mice at specific pathogen free (SPF) level and were supplied from Shanghai Sippr/BK Lab Animal Ltd. (Shanghai, China). For example, 40 animals were obtained and ones in desired health were selected there-from for the experiments. All animals had a certificate of conformity, e.g., with certificate number 0123627. These animals were at the age of about 7 weeks to about 9 weeks at the beginning of the experiments and had the weight of about 18 grams to about 22 grams at the beginning of the experiment. The animals had acclimatization duration of about 5 days to about 7 days. Animals were numbered using their tail number. The animal room was maintained at about 23±2° C., 40%-70% humidity, with alternating light and dark every 12 hours.

Animal foods (SLAC-M01) were purchased from Beijing Ke Ao Xie Li Cooperation Limited (Beijing, China). Sterilized filtration water was used for the experimental animals. During the experiment period, the animals could eat and drink freely.

4. Experimental methods were provided.

4.1 Tumor cells were human HCT-116 colon cancer cells purchased from the Institute of Cell Biology, Chinese Academy of Sciences (Beijing, China). F-12 medium (containing 10% FBS) was used to culture cells in a carbon dioxide incubator at about 37° C., saturated humidity, under 5% $CO_2$ and 95% air. Before inoculation, cells in logarithmic growth phase were collected. After digested by 0.25% trypsin, the cells were washed with PBS once. The cells were resuspended with serum-free medium and counted. Serum-free medium were used for cell resuspension, until the cell concentration was adjusted to about $3\times10^7$ cell/mL.

4.2 Animal inoculation and grouping were performed. Under aseptic conditions, each nude mice was injected with 0.1 mL cell suspension into the right hind leg subcutaneously ($3\times10^6$ cell/mouse). When the size of the tumor grew to have a volume of about 60-150 mm³, nude mice with a similar tumor size and a desirable shape (e.g., with substantially same shape such as a substantially spherical shape, without having irregular shapes or multiple tumors grouped together) were selected and grouped. In the experiment, there were six mice in each group. The grouping situation was listed in Table 3, where IP denotes intraperitoneal injection, and "QD×1" means one injection.

TABLE 3

Animal grouping and inoculation.

| Group No. | Medication | Number of animals | Dosage (mg/kg) | Administration method | Injection |
|---|---|---|---|---|---|
| 1 | D1 | 6 | 400 | IP | QD × 1 |
| 2 | D2 | 6 | 400 | IP | QD × 1 |
| 3 | D3 | 6 | 350 | IP | QD × 1 |
| 4 | D4 | 6 | 300 | IP | QD × 1 |
| 13 | Control | 6 | — | IP | QD × 1 |

The mice in control group were injected with a mixed solution including ethanol, Cremophor EL and normal saline at a ratio of 5:5:90.

4.3 Drug administration and observation of animals were provided.

Nude mice in each group were observed for tumor formation and growth at inoculation sites. The diameters (D) of the tumor nodules were measured three times a week with a circle sizer ruler. In addition, the following formula was applied to calculate the volume of the tumor nodules (V): $V=3/4\pi(D/2)^3$ generally for a spherical shape. Evaluation indexes of antitumor activity were tumor growth inhibition rate TGI (%) and relative tumor proliferation rate T/C (%).

The calculation formula of TGI was: TGI (%)=($V_{control}-V_{Treatment}$)/$V_{control}\times100\%$. The relative tumor volume (RTV) was calculated by: RTV=Vt/V0, where V0 is the tumor volume at the time of group administration, and Vt is the tumor volume at the time of measurement.

Relative tumor proliferation rate T/C (%) was calculated as: T/C (%)=$T_{RTV}/C_{RTV}\times100\%$. $T_{RTV}$ denotes treatment group RTV; and $C_{RTV}$ denotes negative control group RTV. The mice were weighed 3 times every week.

4.4 Clinical symptoms were provided. All clinical symptoms of each animal were recorded at the beginning of the experiments and during the experiments. The observation was performed at the same time every day.

After administration of the test substance, when the weight reduction was >20%, when the animal was dying, or when the tumor volume exceeds about 2800 mm³, the animal were euthanized by applying $CO_2$. The tumor was separated and weighed, an autopsy was performed, and visual inspection was conducted and recorded on whether there were pathological changes in the organs.

4.5 Data and statistical analysis were provided. Unless otherwise indicated, experimental data were presented by Mean±SEM; unpaired T-test was used for comparing between two groups, the result was considered significantly different when P<0.05.

5. Experiment results included the following. (1) The influence of the test compounds on the weight of tumor-bearing mice with human colon cancer HCT-116 was measured. The average weight of the animals in each group is shown in Table 4, where "*" indicates p-value<0.05 versus the control group and "**" indicates p-value<0.01 versus the control group.

TABLE 4

Average weight of the animals in each group after treatment.

| Groups | Dosage (mg/kg) | Day 0 (g) | Day 1 (g) | Day 2 (g) | Day 4 (g) | Day 7 (g) |
|---|---|---|---|---|---|---|
| D1 | 400 | 19.98 ± 0.49 | 19.48 ± 0.58 | 17.45 ± 0.81* | 16.15 ± 1.08** | 19.80 ± 1.40 |
| D2 | 400 | 19.87 ± 0.25 | 19.85 ± 0.28 | 18.17 ± 0.31** | 17.75 ± 0.44** | 18.48 ± 0.40 |
| D3 | 350 | 19.95 ± 0.09 | 19.23 ± 0.31 | 17.70 ± 0.26** | 18.24 ± 0.58* | 19.51 ± 0.48 |
| D4 | 300 | 20.15 ± 0.29 | 19.90 ± 0.19 | 18.48 ± 0.2** | 19.07 ± 0.36 | 19.85 ± 0.38 |
| Control | (NA) | 20.55 ± 0.37 | 20.43 ± 0.45 | 20.07 ± 0.38 | 20.02 ± 0.29 | 19.33 ± 0.26 |

| Groups | Dosage (mg/kg) | Day 9 (g) | Day 11 (g) | Day 14 (g) | Day 16 (g) | Day 18 (g) |
|---|---|---|---|---|---|---|
| D1 | 400 | 20.75 ± 1.05 | 21.25 ± 1.55 | 21.35 ± 1.35* | 21.75 ± 1.25* | 23.30 ± 1.60** |
| D2 | 400 | 19.92 ± 0.45 | 20.42 ± 0.53 | 20.85 ± 0.60* | 21.13 ± 0.51** | 21.63 ± 0.51** |
| D3 | 350 | 20.74 ± 0.38 | 21.12 ± 0.41 | 21.26 ± 0.21** | 22.00 ± 0.40** | 22.58 ± 0.38** |
| D4 | 300 | 20.73 ± 0.29* | 21.05 ± 0.31 | 20.90 ± 0.34** | 21.48 ± 0.34** | 21.95 ± 0.27** |
| Control | (NA) | 19.85 ± 0.23 | 20.23 ± 0.25 | 19.42 ± 0.19 | 19.62 ± 0.29 | 19.68 ± 0.23 |

| Groups | Dosage (mg/kg) | Day 21 (g) | Day 23 (g) | Day 25 (g) | Day 28 (g) | Day 30 (g) |
|---|---|---|---|---|---|---|
| D1 | 400 | 22.30 ± 1.30** | 22.60 ± 1.50* | 23.20 ± 1.70 | 23.80 ± 1.50 | 23.60 ± 1.20 |
| D2 | 400 | 20.72 ± 0.46* | 20.60 ± 0.40 | 20.88 ± 0.48 | 20.18 ± 0.44 | 20.33 ± 0.55 |
| D3 | 350 | 21.98 ± 0.41** | 22.44 ± 0.41** | 22.50 ± 0.53** | 22.12 ± 0.48* | 22.90 ± 0.60 |
| D4 | 300 | 21.63 ± 0.30** | 22.03 ± 0.43** | 22.30 ± 0.49** | 21.88 ± 0.59 | 22.03 ± 0.53 |
| Control | (NA) | 19.30 ± 0.24 | 19.55 ± 0.18 | 20.08 ± 0.30 | 19.75 ± 0.05 | N/A |

TABLE 5

Average rate of weight change of the animals in each group after treatment.

| Groups | Dosage (mg/kg) | Day 0 (%) | Day 1 (%) | Day 2 (%) | Day 4 (%) | Day 7 (%) |
|---|---|---|---|---|---|---|
| D1 | 400 | 0.00 | −2.55 ± 0.77 | −12.18 ± 2.63** | −18.58 ± 4.66** | −4.23 ± 3.77 |
| D2 | 400 | 0.00 | −0.08 ± 0.74 | −8.54 ± 1.31** | −10.63 ± 2.13** | −6.98 ± 1.43 |
| D3 | 350 | 0.00 | −3.59 ± 0.66 | −11.25 ± 0.96** | −8.10 ± 2.84 | −1.68 ± 2.50 |
| D4 | 300 | 0.00 | −1.17 ± 1.27 | −8.18 ± 1.56** | −5.33 ± 1.78 | −1.43 ± 1.92 |
| Control | (NA) | 0.00 | −0.60 ± 0.59 | −2.35 ± 0.75 | −2.55 ± 0.82 | −5.85 ± 1.13 |

| Groups | Dosage (mg/kg) | Day 9 (%) | Day 11 (%) | Day 14 (%) | Day 16 (%) | Day 18 (%) |
|---|---|---|---|---|---|---|
| D1 | 400 | 0.42 ± 1.92 | 2.77 ± 4.27 | 3.29 ± 3.29 | 5.24 ± 2.74 | 12.70 ± 4.20** |
| D2 | 400 | 0.21 ± 1.42 | 2.72 ± 1.85 | 4.87 ± 2.08** | 6.32 ± 1.65** | 8.83 ± 1.43** |
| D3 | 350 | 4.50 ± 1.93* | 6.38 ± 1.68* | 7.12 ± 1.19** | 10.78 ± 0.88** | 13.71 ± 0.63** |
| D4 | 300 | 2.91 ± 0.55** | 4.47 ± 0.52* | 3.72 ± 0.73** | 6.62 ± 0.79** | 8.99 ± 1.38** |
| Control | (NA) | −3.30 ± 1.54 | −1.39 ± 2.07 | −5.39 ± 1.69 | −4.38 ± 2.27 | −4.05 ± 2.20 |

| Groups | Dosage (mg/kg) | Day 21 (%) | Day 23 (%) | Day 25 (%) | Day 28 (%) | Day 30 (%) |
|---|---|---|---|---|---|---|
| D1 | 400 | 7.90 ± 2.90* | 9.32 ± 3.82* | 12.20 ± 4.70 | 15.14 ± 3.64 | 14.22 ± 2.22 |
| D2 | 400 | 4.22 ± 1.23** | 3.66 ± 1.05** | 5.07 ± 1.44 | 1.57 ± 1.50 | 2.28 ± 1.75 |
| D3 | 350 | 10.72 ± 1.6** | 13.08 ± 2.31** | 13.34 ± 2.34** | 11.44 ± 2.29** | 15.37 ± 2.93 |
| D4 | 300 | 7.41 ± 1.37** | 9.37 ± 1.82** | 10.69 ± 2.14** | 8.62 ± 2.68 | 9.36 ± 2.21 |
| Control | (NA) | −5.94 ± 2.02 | −3.59 ± 1.66 | −0.97 ± 2.53 | −2.68 ± 5.27 | N/A |

As indicated by data in the Tables 4 and 5, after intraperitoneal injecting each compound into the tumor-bearing nude mice with HCT-116 colon cancer xenografts, D1 group with a dose of 400 mg/kg of D1 compound showed body weight was significantly decreased on Day 4 after D1 drug administration, followed by steady weight growth in later days. After that, the weight was significantly increased comparing with the control group. There were no significant differences between other drug-treated groups and the control group, indicating no toxicity of the three compounds (D2, D3 and D4) in tumor-bearing mice.

(2) The effect of the test compounds on the tumor volume of HCT-116 human colon cancer xenografts in nude mice was measured. Table 6 shows the detailed data about tumor volumes of each group, where "*" indicates p-value<0.05 versus the control group and "**" indicates p-value<0.01 versus the control group.

TABLE 6

Effects of the four cytidine derivative dimers on HCT-116 human colon cancer xenografts.

| Groups | Dosage (mg/kg) | Day 0 (mm$^3$) | Day 1 (mm$^3$) | Day 2 (mm$^3$) | Day 4 (mm$^3$) |
|---|---|---|---|---|---|
| D1 | 400 | 39.36 ± 6.16** | 58.20 ± 17.45** | 58.20 ± 17.45** | 37.24 ± 9.27** |
| D2 | 400 | 53.09 ± 9.33** | 50.78 ± 14.16** | 55.89 ± 18.82** | 45.96 ± 20.25** |
| D3 | 350 | 38.77 ± 4.33** | 36.40 ± 3.98** | 36.40 ± 3.98** | 23.00 ± 3.08** |
| D4 | 300 | 44.09 ± 5.99** | 52.03 ± 12.91** | 52.03 ± 12.91** | 37.37 ± 10.46** |
| Control | (NA) | 109.55 ± 8.60 | 180.51 ± 9.97 | 221.87 ± 11.44 | 296.98 ± 22.98 |

| Groups | Dosage (mg/kg) | Day 7 (mm$^3$) | Day 9 (mm$^3$) | Day 11 (mm$^3$) | Day 14 (mm$^3$) |
|---|---|---|---|---|---|
| D1 | 400 | 36.82 ± 28.63** | 50.63 ± 36.49** | 101.02 ± 78.57** | 285.66 ± 237.94* |
| D2 | 400 | 35.87 ± 21.79** | 30.75 ± 16.74** | 57.29 ± 33.0** | 116.87 ± 66.85** |
| D3 | 350 | 12.62 ± 3.10** | 12.62 ± 3.10** | 14.28 ± 3.69** | 36.98 ± 4.82** |
| D4 | 300 | 25.46 ± 8.17** | 22.50 ± 5.31** | 26.19 ± 5.79** | 70.28 ± 18.37** |
| Control | (NA) | 432.47 ± 39.48 | 590.34 ± 60.83 | 976.15 ± 83.07 | 1440.15 ± 144.73 |

| Groups | Dosage (mg/kg) | Day 16 (mm$^3$) | Day 18 (mm$^3$) | Day 21 (mm$^3$) | Day 23 (mm$^3$) |
|---|---|---|---|---|---|
| D1 | 400 | 495.95 ± 408.8** | 647.07 ± 503.28** | 1017.61 ± 749.53 | 1017.61 ± 749.53 |
| D2 | 400 | 169.73 ± 88.15** | 262.10 ± 111.14** | 489.13 ± 174.91 | 501.98 ± 170.25 |
| D3 | 350 | 80.10 ± 11.07** | 120.40 ± 23.44** | 204.05 ± 36.25 | 229.06 ± 36.15 |
| D4 | 300 | 142.77 ± 49.34** | 228.58 ± 76.92** | 375.06 ± 86.27 | 420.73 ± 76.08 |
| Control | (NA) | 1811.14 ± 119.30 | 1998.33 ± 136.40 | 2444.84 ± 167.64 | 2361.69 ± 146.79 |

| Groups | Dosage (mg/kg) | Day 25 (mm$^3$) | Day 28 (mm$^3$) | Day 30 (mm$^3$) |
|---|---|---|---|---|
| D1 | 400 | 1044.35 ± 722.80 | 1296.79 ± 847.87 | 1589.29 ± 983.15 |
| D2 | 400 | 569.05 ± 189.18 | 689.78 ± 203.52 | 900.52 ± 250.44 |
| D3 | 350 | 266.11 ± 39.63 | 347.17 ± 60.84 | 479.01 ± 75.54 |

TABLE 6-continued

Effects of the four cytidine derivative dimers on HCT-116 human colon cancer xenografts.

| | | | | |
|---|---|---|---|---|
| D4 | 300 | 491.29 ± 83.78 | 608.08 ± 85.37 | 781.78 ± 105.33 |
| Control | (NA) | 2582.36 ± 155.95 | 2689.30 ± 116.86 | N/A |

As indicated by the detailed data of tumor volumes of each group in Table 6, the four disclosed cytidine derivative dimers significantly inhibited the growth of HCT-116 human colon cancer xenografts.

(3) Tumor growth inhibition rate (TGI %) of the test compounds on HCT-116 human colon cancer xenografts was measured. The tumor growth inhibition rate (TGI %) of the test compounds D1-D4 on HCT-116 human colon cancer xenografts are shown as follows in Table 7.

TABLE 7

Tumor growth inhibition rate (TGI %) after treatment with four cytidine derivative dimers.

| Group | Dosage (mg/kg) | Day 0 (TGI %) | Day 1 (TGI %) | Day 2 (TGI %) | Day 4 (TGI %) | Day 7 (TGI %) |
|---|---|---|---|---|---|---|
| D1 | 400 | 0.00 | 67.76 | 73.77 | 87.46 | 91.49 |
| D2 | 400 | 0.00 | 71.87 | 74.81 | 84.53 | 91.71 |
| D3 | 350 | 0.00 | 79.83 | 83.59 | 92.26 | 97.08 |
| D4 | 300 | 0.00 | 71.17 | 76.55 | 87.42 | 94.11 |

| Group | Dosage (mg/kg) | Day 9 (TGI %) | Day 11 (TGI %) | Day 14 (TGI %) | Day 16 (TGI %) | Day 18 (TGI %) |
|---|---|---|---|---|---|---|
| D1 | 400 | 91.42 | 89.65 | 80.16 | 72.62 | 67.62 |
| D2 | 400 | 94.79 | 94.13 | 91.88 | 90.63 | 86.88 |
| D3 | 350 | 97.86 | 98.54 | 97.43 | 95.58 | 93.97 |
| D4 | 300 | 96.19 | 97.32 | 95.12 | 92.12 | 88.56 |

| Group | Dosage (mg/kg) | Day 21 (TGI %) | Day 23 (TGI %) | Day 25 (TGI %) | Day 28 (TGI %) | Day 30 (TGI %) |
|---|---|---|---|---|---|---|
| D1 | 400 | 58.38 | 56.91 | 59.56 | 51.78 | 43.36 |
| D2 | 400 | 79.99 | 78.74 | 77.96 | 74.35 | 67.91 |
| D3 | 350 | 91.65 | 90.30 | 89.70 | 87.09 | 82.93 |
| D4 | 300 | 84.66 | 82.19 | 80.98 | 77.39 | 72.14 |

The tumor inhibition rate of compound D1 group with 400 mg/kg dosage reached to a maximum of 91.49% on Day 7. The tumor inhibition rate of compound D2 group with 400 mg/kg dosage reached to a maximum of 94.79% on Day 9. The tumor inhibition rate of compound D3 group with 350 mg/kg dosage reached to a maximum of 98.54% on Day 11. The tumor inhibition rate of compound D4 group with 300 mg/kg dosage reached to a maximum of 97.32% on Day 11.

(4) Effects of four test compounds on relative tumor volume (RTV) of HCT-116 human colon cancer xenografts were provided.

Table 8 shows the significant effects of D1-D4 test compounds on relative tumor volume (RTV) of HCT-116 human colon cancer xenografts, where "*" indicates p-value<0.05 versus the control group and "**" indicates p-value<0.01 versus the control group.

TABLE 8

Effects of four cytidine derivative dimers on RTV of HCT-116 human colon cancer xenografts.

| Groups | Dosage (mg/kg) | Day 0 (RTV) | Day 1 (RTV) | Day 2 (RTV) | Day 4 (RTV) | Day 7 (RTV) |
|---|---|---|---|---|---|---|
| D1 | 400 | 1.00 | 1.35 ± 0.24 | 1.35 ± 0.24* | 0.89 ± 0.12** | 1.16 ± 0.79* |
| D2 | 400 | 1.00 | 0.89 ± 0.10** | 0.95 ± 0.15** | 0.73 ± 0.19** | 0.52 ± 0.23** |
| D3 | 350 | 1.00 | 0.98 ± 0.12** | 0.98 ± 0.12** | 0.65 ± 0.10** | 0.34 ± 0.06** |
| D4 | 300 | 1.00 | 1.12 ± 0.12 | 1.12 ± 0.12 | 0.79 ± 0.11* | 0.55 ± 0.10* |
| Control | (NA) | 1.00 | 1.68 ± 0.13 | 2.07 ± 0.16 | 2.76 ± 0.24 | 4.09 ± 0.53 |

| Groups | Dosage (mg/kg) | Day 9 (RTV) | Day 11 (RTV) | Day 14 (RTV) | Day 16 (RTV) | Day 18 (RTV) |
|---|---|---|---|---|---|---|
| D1 | 400 | 1.61 ± 0.98 | 3.18 ± 2.18* | 8.88 ± 6.75 | 15.44 ± 11.56 | 20.37 ± 13.96 |
| D2 | 400 | 0.46 ± 0.17** | 0.87 ± 0.35** | 1.80 ± 0.69** | 2.66 ± 0.88** | 4.20 ± 1.02** |
| D3 | 350 | 0.32 ± 0.05** | 0.37 ± 0.09** | 1.00 ± 0.00** | 2.17 ± 0.14** | 3.16 ± 0.39** |

TABLE 8-continued

Effects of four cytidine derivative dimers on RTV of HCT-116 human colon cancer xenografts.

| D4 | 300 | 0.55 ± 0.12* | 0.69 ± 0.20* | 1.81 ± 0.54* | 3.29 ± 0.82* | 5.11 ± 1.12* |
|---|---|---|---|---|---|---|
| Control | (NA) | 5.61 ± 0.83 | 9.22 ± 1.16 | 13.84 ± 2.21 | 17.26 ± 2.18 | 19.09 ± 2.45 |

| Groups | Dosage (mg/kg) | Day 21 (RTV) | Day 23 (RTV) | Day 25 (RTV) | Day 28 (RTV) | Day 30 (RTV) |
|---|---|---|---|---|---|---|
| D1 | 400 | 32.34 ± 20.40 | 32.34 ± 20.40 | 33.53 ± 19.21 | 42 ± 22 | 51.88 ± 24.88 |
| D2 | 400 | 8.09 ± 1.52 | 8.48 ± 1.37 | 9.62 ± 1.48 | 12.03 ± 1.50 | 15.85 ± 1.92 |
| D3 | 350 | 5.55 ± 0.66 | 6.21 ± 0.61 | 7.22 ± 0.53 | 9.28 ± 0.73 | 12.93 ± 0.90 |
| D4 | 300 | 8.73 ± 1.39 | 9.89 ± 1.30 | 11.61 ± 1.51 | 14.73 ± 2.18 | 19.08 ± 2.98 |
| Control | (NA) | 23.41 ± 3.10 | 19.77 ± 1.73 | 21.62 ± 1.86 | 21.13 ± 1.62 | N/A |

(5) Effects of four test compounds on relative tumor proliferation rate (T/C %) of HCT-116 human colon cancer xenografts were provided. Table 9 shows the effects of D1-D4 test compounds on relative tumor proliferation rate of HCT-116 human colon cancer xenografts.

TABLE 9

Effects of four cytidine derivative dimers on relative tumor proliferatiom rate (T/C %) of HCT-116 human colon cancer xenografts.

| Groups | Dosage (mg/kg) | Day 0 (T/C %) | Day 1 (T/C %) | Day 2 (T/C %) | Day 4 (T/C %) | Day 7 (T/C %) |
|---|---|---|---|---|---|---|
| D1 | 400 | 0.00 | 80.13 | 65.15 | 32.20 | 28.36 |
| D2 | 400 | 0.00 | 50.15 | 40.78 | 25.19 | 16.63 |
| D3 | 350 | 0.00 | 60.98 | 49.58 | 23.26 | 6.76 |
| D4 | 300 | 0.00 | 77.07 | 66.48 | 43.31 | 31.86 |

| Groups | Dosage (mg/kg) | Day 9 (T/C %) | Day 11 (T/C %) | Day 14 (T/C %) | Day 16 (T/C %) | Day 18 (T/C %) |
|---|---|---|---|---|---|---|
| D1 | 400 | 28.77 | 34.47 | 64.15 | 89.47 | 106.69 |
| D2 | 400 | 14.41 | 16.77 | 18.33 | 21.64 | 21.99 |
| D3 | 350 | 4.71 | 3.41 | 5.78 | 10.49 | 16.55 |
| D4 | 300 | 30.55 | 25.94 | 32.83 | 37.96 | 26.76 |

| Groups | Dosage (mg/kg) | Day 21 (T/C %) | Day 23 (T/C %) | Day 25 (T/C %) | Day 28 (T/C %) | Day 30 (T/C %) |
|---|---|---|---|---|---|---|
| D1 | 400 | 138.14 | 163.55 | 155.09 | 198.76 | 209.10 |
| D2 | 400 | 34.57 | 42.87 | 44.51 | 56.94 | 63.87 |
| D3 | 350 | 23.70 | 31.41 | 33.40 | 43.93 | 52.09 |
| D4 | 300 | 37.28 | 50.04 | 53.68 | 69.72 | 76.91 |

The relative tumor proliferation rate of compound D1 group with 400 mg/kg dosage reached to a minimum of 28.36% on Day 7. The relative tumor proliferation rate of compound D2 group with 400 mg/kg dosage reached to a minimum of 14.41% on Day 9. The relative tumor proliferation rate of compound D3 group with 350 mg/kg dosage reached to a minimum of 3.41% on Day 11. The relative tumor proliferation rate of compound D4 group with 300 mg/kg dosage reached to a minimum of 25.94% on Day 11.

In the tumor inhibition experiment of the series of compounds on HCT-116 human colon cancer xenografts, compounds D2, D3, D4 exhibited higher tumor inhibition rates on HCT-116 human colon cancer xenografts. After a one-time intraperitoneal drug administration, there had been a significant tumor inhibition effect without obvious influence on the body weight of the animals, indicating a high anti-tumor activity of the disclosed cytidine derivative dimers with very low toxic side effects.

As such, various embodiments provide cytidine derivative dimers (including, for example, those listed in Table 1) and/or pharmaceutically acceptable salt thereof, which can be used as effective ingredients in therapeutic (or sometimes prophylactic) agents for treating tumors in animals and/or humans. Accordingly, a therapeutic method for treating tumors using the disclosed cytidine derivative dimers and/or their salts can include: administering to a patient (e.g., including an animal or a human) an effective amount of such therapeutic (or sometimes prophylactic) agent. For example, the therapeutic (or sometimes prophylactic) agent can be a tumor inhibiting drug. Further, methods of producing the disclosed cytidine derivative dimers and/or their salts are provided. Additionally, methods of producing a therapeutic or prophylactic agent including the disclosed cytidine derivative dimers and/or their salts are provided. For example, the therapeutic or prophylactic agent including the disclosed cytidine derivative dimers and/or their salts may include the disclosed pharmaceutical composition.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the claims.

What is claimed is:

1. A method of inhibiting a colon tumor in a host in need thereof, comprising: administering to a subject with a therapeutically effective amount of a cytidine derivative dimer of formula (I) or a pharmaceutically acceptable salt form thereof,

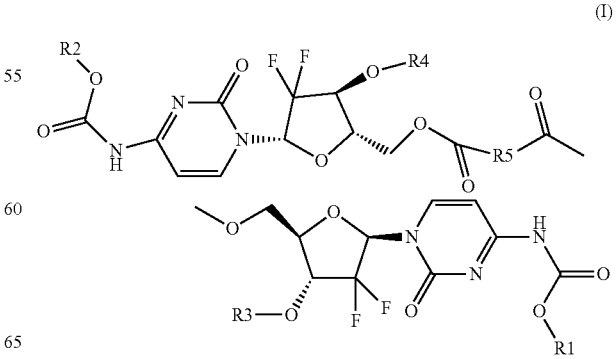

(I)

wherein:

R1 is $C_1$-$C_{10}$ alkyl, $C_1$-$C_{10}$ substituted alkyl, —$(CH_2)_n$-Ph, or substituted —$(CH_2)_n$-Ph, n being an integer from 0 to 10, and Ph being phenyl;

a carbon chain of the $C_1$-$C_{10}$ substituted alkyl is independently substituted by a substituent selected from a group consisting of halogen, cyano group, nitro group, hydroxyl group, and carboxyl group; and a carbon chain or a phenyl ring of the substituent —$(CH_2)_n$-Ph is independently substituted by a substituent selected from a group consisting of halogen, cyano group, nitro group, hydroxyl group, and carboxyl group;

wherein:

R2 is $C_1$-$C_{10}$ alkyl, $C_1$-$C_{10}$ substituted alkyl, —$(CH_2)_n$-Ph, or substituted —$(CH_2)_n$-Ph, n being an integer from 0 to 10, and Ph being phenyl;

a carbon chain of the $C_1$-$C_{10}$ substituted alkyl is independently substituted by a substituent selected from a group consisting of halogen, cyano group, nitro group, hydroxyl group, and carboxyl group; and a carbon chain or a phenyl ring of the substituted —$(CH_2)_n$-Ph is independently substituted by a substituent selected from a group consisting of halogen, cyano group, nitro group, hydroxyl group, and carboxyl group; and wherein:

R3 is hydrogen, alkoxycarbonyl or substituted alkoxycarbonyl, wherein a substituent of the substituted alkoxycarbonyl is selected from a group consisting of halogen, cyano group, nitro group, hydroxyl group, and carboxyl group;

R4 is hydrogen, alkoxycarbonyl or substituted alkoxycarbonyl, wherein a substituent of the substituted alkoxycarbonyl is selected from a group consisting of halogen, cyano group, nitro group, hydroxyl group, and carboxyl group; and R5 is —$(CH_2)_n$—, n being an integer from 1 to 15; or substituted —$(CH_2)_n$—with a substituent on a carbon chain thereof, n being an integer from 1 to 15, and the substituent being selected from a group consisting of phenyl group, substituted phenyl group, cyano group, nitro group, hydroxyl group, and carboxyl group; or —$(CH_2)_{n1}$—O—$(CH_2)_{n2}$-Ph-, and n1 and n2 being an integer from 0 to 3.

2. The method according to claim 1, wherein R3 is hydrogen and R4 is hydrogen.

3. The method according to claim 2, wherein R1 and R2 are the same.

4. The method according to claim 1, further comprising:
administering a subject in need thereof and having a colon cancer with a therapeutically effective amount of the cytidine derivative dimer or a pharmaceutically acceptable salt form thereof.

5. The method according to claim 1, wherein R1 and R2 are the same.

6. A method for preparing a cytidine derivative dimer, comprising:
preparing a compound having a general formula (II); and

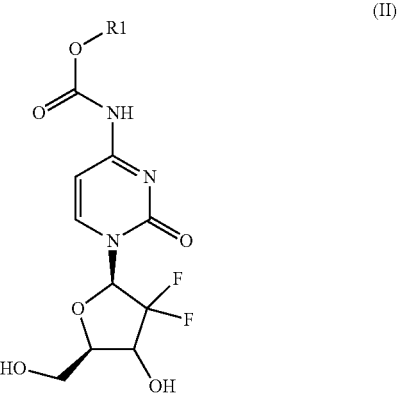

(II)

preparing a compound having a general formula (III);

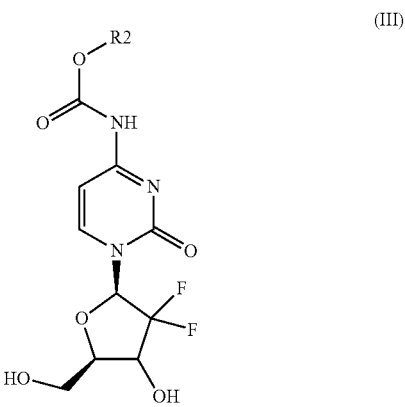

(III)

mixing the compound having the general formula (II) with sodium carbonate to add to a system including 1,4-dioxane and water, adding $(Boc)_2O$ into the system for a reaction, and when the reaction is measured to be completed to provide a reaction product, extracting and washing the reaction product, and then drying and concentrating to form a dried solid under a reduced pressure, purifying the dried solid by column chromatography to afford an intermediate compound;

adding the intermediate compound into chloroform, adding in pyridine and cyclic carboxylic anhydrides $R_5(CO)_2O$ for an overnight reaction, concentrating to yield a viscous oil, and purifying the viscous oil by column chromatography to obtain a compound with a general formula (IV):

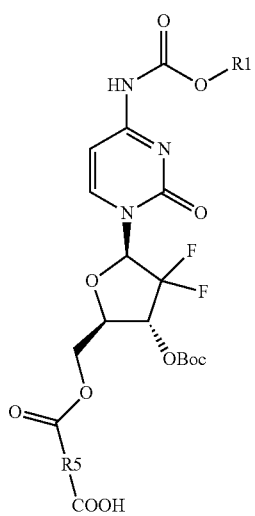

(IV)

mixing and adding the compound having the general formula (IV), the compound having the general formula (III), and N,N'-dicyclohexylcarbodiimide (DCC) to methylene chloride;

adding in 4-dimethylaminopyridine (DMAP) for a reaction, when the reaction is measured to be completed, washing, drying, and concentrating the reaction mixture to form a dried solid under a reduced pressure; and adding trifluoroacetic acid (TFA) and dichloromethane (DCM) to the dried solid, stirring at room temperature, cooling in an ice bath, and filtering to provide a white solid, concentrating the white solid into a viscous oil, and purifying the viscous oil by column chromatography to produce the cytidine derivative dimer;

wherein the prepared cytidine derivative dimer has a general formula (I), wherein:
R2 is $C_1$-$C_{10}$ alkyl, $C_1$-$C_{10}$ substituted alkyl, —$(CH_2)_n$-Ph, or substituted —$(CH_2)_n$-Ph, n being an integer from 0 to 10, and Ph being phenyl;

a carbon chain of the $C_1$-$C_{10}$ substituted alkyl is independently substituted by a substituent selected from a group consisting of halogen, cyano group, nitro group, hydroxyl group, and carboxyl group; and a carbon chain or a phenyl ring of the substituted —$(CH_2)_n$-Ph is independently substituted by a substituent selected from a group consisting of halogen, cyano group, nitro group, hydroxyl group, and carboxyl group;

wherein:
R3 is hydrogen, alkoxycarbonyl or substituted alkoxycarbonyl, and a substituent of the substituted alkoxycarbonyl is selected from a group consisting of halogen, cyano group, nitro group, hydroxyl group, and carboxyl group;

R4 is hydrogen, alkoxycarbonyl or substituted alkoxycarbonyl, and a substituent of the substituted alkoxycarbonyl is selected from a group consisting of halogen, cyano group, nitro group, hydroxyl group, and carboxyl group; and wherein:
R5 is —$(CH_2)_n$—, n being an integer from 1 to 15; or substituted —$(CH_2)_n$— with a substituent on a carbon chain thereof, n being an integer from 1 to 15, and the substituent being selected from a group consisting of phenyl group, substituted phenyl group, cyano group, nitro group, hydroxyl group, and carboxyl group; or —$(CH_2)_{n1}$—O—$(CH_2)_{n2}$-Ph-, n1 and n2 being an integer from 0 to 3.

7. The method according to claim 6, wherein R3 is hydrogen and R4 is hydrogen.

8. The method according to claim 6, wherein R1 and R2 are the same.

9. A method for preparing a cytidine derivative dimer, comprising:

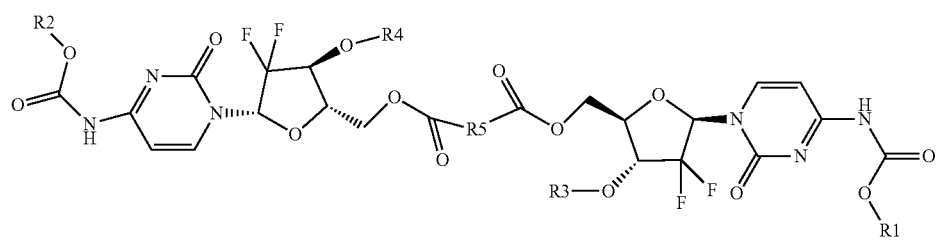

(I)

wherein:
R1 is $C_1$-$C_{10}$ alkyl, $C_1$-$C_{10}$ substituted alkyl, —$(CH_2)_n$-Ph, or substituted —$(CH_2)_n$-Ph, n being an integer from 0 to 10, and Ph being phenyl;

a carbon chain of the $C_1$-$C_{10}$ substituted alkyl is independently substituted by a substituent selected from a group consisting of halogen, cyano group, nitro group, hydroxyl group, and carboxyl group; and a carbon chain or a phenyl ring of the substituted —$(CH_2)_n$-Ph is independently substituted by a substituent selected from a group consisting of halogen, cyano group, nitro group, hydroxyl group, and carboxyl group;

adding tert-butyldimethylsilyl chloride (TB SCL) to 2'-deoxy-2', 2'-difluoro-cytidine hydrochloride and imidazole in anhydrous pyridine to obtain a first compound;

adding butyl chloroformate or tert-butyl chloroformate to a reaction system including dichloromethane (DCM), pyridine, and the first compound to produce a second compound;

adding triethylamine trihydrofluoride to the second compound for an overnight reaction, stripping a solvent of the overnight reaction product to yield a solid, and purifying the solid by column chromatography to obtain a third compound having a general formula (V);

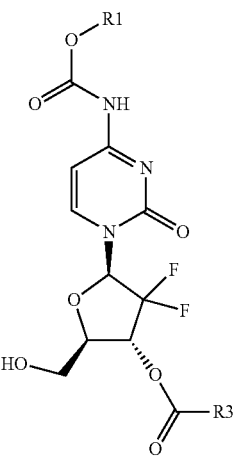

(V)

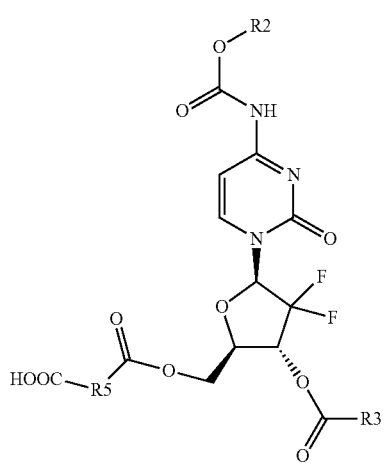

(VI)

adding pyridine and anhydride corresponding to R5 to the third compound in chloroform for an overnight reaction to obtain a reaction mixture, concentrating the reaction mixture to provide a viscous oily product, purifying the viscous oily product to obtain a fourth compound having a general formula (VI);

dissolving the third compound, the fourth compound, and N,N'-dicyclohexylcarbodiimide (DCC) in dichloromethane and adding in 4-dimethylaminopyridine to obtain a mixture;

washing, drying, and concentrating the mixture to obtain a resulting material; and purifying the resulting material by column chromatography to produce a cytidine derivative dimer having a general formula (I),

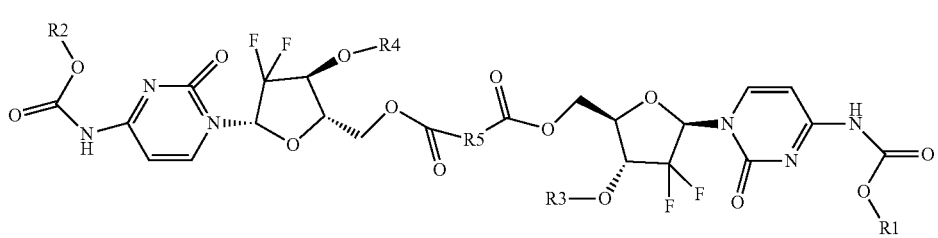

(I)

wherein:
R1 and R2 are the same, R3 and R4 are the same, and R5 is $-(CH_2)_n-$, n being an integer from 1 to 15.

10. The method according to claim 9, wherein R3 and R4 are n-butoxycarbonyl.

11. The method according to claim 10, wherein R1 and R2 are n-butyl.

12. The method according to claim 10, wherein R1 and R2 are tert-butyl.

* * * * *